US012793123B1

United States Patent
(12) United States Patent
Mortensen et al.
(10) Patent No.: US 12,793,123 B1
(45) Date of Patent: Nov. 10, 2026

(54) SYSTEMS AND METHODS FOR ANALYZING ADVERSE EVENTS OF A SOURCE FILE AND ARRANGING THE ADVERSE EVENTS ON A USER INTERFACE

(71) Applicant: Veeva Systems Inc., Pleasanton, CA (US)

(72) Inventors: Marius K. Mortensen, Burlington (CA); Asaf Roll, Richmond Hill (CA); Florian Emmanuel Bernard Gilbert Letourneux, Rennes (FR)

(73) Assignee: Veeva Systems Inc.

( * ) Notice: Subject to any disclaimer, the term of this patent is extended or adjusted under 35 U.S.C. 154(b) by 0 days.

(21) Appl. No.: 17/704,742

(22) Filed: Mar. 25, 2022

Related U.S. Application Data

(63) Continuation-in-part of application No. 17/390,059, filed on Jul. 30, 2021, now Pat. No. 11,907,305.

(60) Provisional application No. 63/220,227, filed on Jul. 9, 2021.

(51) Int. Cl.
*G06F 16/2455* (2019.01)
*G06F 3/0481* (2022.01)
*G06F 16/9038* (2019.01)
*G06Q 30/0601* (2023.01)
*G16H 20/00* (2018.01)

(52) U.S. Cl.
CPC ....... *G06Q 30/0641* (2013.01); *G06F 3/0481* (2013.01); *G06F 16/24556* (2019.01); *G06F 16/9038* (2019.01); *G06Q 30/0603* (2013.01); *G16H 20/00* (2018.01)

(58) Field of Classification Search
CPC ....................... G06F 16/24556; G06F 16/9038
USPC ........................................................ 707/780
See application file for complete search history.

(56) References Cited

U.S. PATENT DOCUMENTS 6,219,674 B1 4/2001 Classen
6,374,241 B1 * 4/2002 Lamburt ................ G06F 16/25 707/999.005
7,146,399 B2 12/2006 Fox et al.
(Continued)

FOREIGN PATENT DOCUMENTS

WO 2016112025 A1 7/2016

OTHER PUBLICATIONS

Oracle Argus Safety, User's Guide, Release 8.1.2, E93471-01, Feb. 2018.
(Continued)

*Primary Examiner* — Tony Mahmoudi
*Assistant Examiner* — Michael Le

(57) ABSTRACT

A method for generating a first case including receiving adverse event information, generating case information of the first case, generating a priority of the case based on the type of the event, selecting a second case which is a potential duplicate of the first case from a database, and providing the case information of the first case and the second case to a user computing device to be displayed on user interface. The user interface displays the case information of the first case adjacent to the case information of the second case and includes a button selectable to indicate the first case is not a duplicate of the second case. The method further includes generating, in response to receiving an indication of a selection of the button, the first case including the case information of the first case.

15 Claims, 14 Drawing Sheets

(56) References Cited

U.S. PATENT DOCUMENTS 7,152,060 B2 * 12/2006 Borthwick ........ G06F 16/24578 707/774
7,209,550 B1 4/2007 Rapaport et al.
7,366,675 B1 4/2008 Walker et al.
7,379,934 B1 5/2008 Forman et al.
7,403,942 B1 * 7/2008 Bayliss ................. G06F 16/215 707/999.005
7,451,096 B2 11/2008 Rucker
7,461,006 B2 12/2008 Gogolak
7,542,961 B2 6/2009 Gogolak
7,860,844 B2 * 12/2010 Ebaugh .................. G06Q 10/10 707/711
8,112,441 B2 * 2/2012 Ebaugh ............... G06F 16/2228 707/780
8,180,779 B2 5/2012 Horowitz et al.
8,266,168 B2 * 9/2012 Bayliss ................. G06F 16/215 707/758
8,943,076 B2 1/2015 Stewart et al.
9,305,267 B2 4/2016 Tatonetti et al.
9,336,286 B2 * 5/2016 Woody .................. G06F 16/248
9,501,539 B2 11/2016 Joshi et al.
9,779,146 B2 * 10/2017 Thatavarthy .......... G06F 16/168
10,169,607 B1 1/2019 Sheth et al.
10,431,330 B2 10/2019 Lal et al.
10,510,440 B1 * 12/2019 Jose ....................... G16H 10/60
10,650,808 B1 * 5/2020 Platt ....................... G16H 10/60
10,811,125 B2 10/2020 Bao et al.
10,873,456 B1 12/2020 Dods et al.
10,991,457 B1 * 4/2021 Hallemeier ............ G16H 40/20
11,106,692 B1 * 8/2021 Guetta .................. G06F 16/248
11,257,572 B1 2/2022 Narke et al.
11,302,426 B1 4/2022 Winlo et al.
11,424,030 B1 8/2022 Saffouri
2001/0032100 A1 10/2001 Mahmud et al.
2001/0051879 A1 * 12/2001 Johnson ................ H04L 63/102 707/999.001
2002/0007284 A1 * 1/2002 Schurenberg .......... G16H 10/60 705/2
2002/0032581 A1 3/2002 Reitberg
2002/0083080 A1 6/2002 Classen
2002/0087362 A1 7/2002 Cobb et al.
2002/0095261 A1 7/2002 Gut et al.
2002/0165845 A1 11/2002 Gogolak
2002/0165852 A1 11/2002 Gogolak
2002/0165853 A1 11/2002 Gogolak
2002/0169637 A1 11/2002 Akers et al.
2003/0046110 A1 3/2003 Gogolak
2003/0046280 A1 * 3/2003 Rotter ..................... G16Z 99/00
2003/0060688 A1 3/2003 Ciarniello et al.
2003/0065537 A1 4/2003 Evans
2003/0097359 A1 * 5/2003 Ruediger .............. G06F 16/215
2003/0126156 A1 * 7/2003 Stoltenberg ........... G06F 16/215
2003/0140044 A1 7/2003 Mok et al.
2004/0019501 A1 * 1/2004 White .................... G16H 15/00 705/2
2004/0019593 A1 * 1/2004 Borthwick ........ G06F 16/24578
2004/0078216 A1 4/2004 Toto
2004/0117126 A1 6/2004 Fetterman et al.
2004/0158475 A1 8/2004 Juzeszyn et al.
2004/0249789 A1 * 12/2004 Kapoor ................. G06F 16/215
2005/0197547 A1 9/2005 Trinks et al.
2005/0234745 A1 10/2005 Schoenberg
2005/0234843 A1 10/2005 Beckius et al.
2006/0242037 A1 10/2006 Tanimura et al.
2007/0016450 A1 1/2007 Bhora et al.
2007/0061393 A1 3/2007 Moore
2007/0106754 A1 5/2007 Moore
2007/0124302 A1 5/2007 Korn et al.
2008/0040151 A1 2/2008 Moore
2008/0046286 A1 * 2/2008 Halsted .................. G16H 15/00 705/2
2008/0077573 A1 * 3/2008 Weinberg .......... G06F 16/24558 707/999.005
2008/0082582 A1 4/2008 Jung et al.
2008/0162580 A1 * 7/2008 Ben Harush .......... G06F 16/335
2008/0313204 A1 12/2008 Schultz et al.
2009/0024639 A1 1/2009 Steinmann
2009/0043752 A1 2/2009 Kenedy et al.
2009/0055378 A1 2/2009 Alecu et al.
2009/0083334 A1 3/2009 Smith
2009/0089317 A1 * 4/2009 Ford ..................... G06F 16/288 707/999.102
2009/0112882 A1 4/2009 Maresh et al.
2009/0125331 A1 5/2009 Pamsgaard et al.
2009/0158200 A1 6/2009 Palahnuk et al.
2009/0164781 A1 6/2009 Bouchard
2009/0222539 A1 9/2009 Lewis et al.
2009/0319299 A1 12/2009 Vries et al.
2010/0223294 A1 9/2010 Winslow
2010/0268543 A1 10/2010 George et al.
2010/0312799 A1 * 12/2010 Harush ................. G06F 16/335 707/E17.014
2010/0332554 A1 12/2010 Blair et al.
2011/0029488 A1 2/2011 Fuerst et al.
2011/0040791 A1 2/2011 Kenedy et al.
2011/0145018 A1 6/2011 Fotsch et al.
2011/0202370 A1 8/2011 Green et al.
2011/0213625 A1 9/2011 Joao
2011/0246236 A1 10/2011 Green et al.
2011/0295621 A1 12/2011 Farooq et al.
2011/0301982 A1 12/2011 Green et al.
2012/0059662 A1 3/2012 Huisman, Jr.
2012/0066000 A1 * 3/2012 Opfer ..................... G16H 70/20 705/3
2012/0072464 A1 * 3/2012 Cohen .................. G06F 16/215 707/E17.044
2012/0089418 A1 4/2012 Kamath et al.
2012/0102040 A1 4/2012 Battle et al.
2012/0143776 A1 6/2012 Jaffe et al.
2012/0166218 A1 6/2012 Reiner
2012/0209625 A1 8/2012 Armstrong et al.
2012/0239413 A1 9/2012 Mathur et al.
2012/0239612 A1 9/2012 George et al.
2012/0265655 A1 10/2012 Stroh
2012/0323576 A1 12/2012 Wang et al.
2013/0046558 A1 2/2013 Landi et al.
2013/0166573 A1 6/2013 Vaitheeswaran et al.
2013/0179187 A1 7/2013 Jackson et al.
2013/0191161 A1 7/2013 Churchwell et al.
2013/0219011 A1 8/2013 White
2013/0297661 A1 11/2013 Jagota
2014/0028464 A1 1/2014 Garibaldi
2014/0058744 A1 2/2014 Nadarajah et al.
2014/0067407 A1 3/2014 Sathe et al.
2014/0081667 A1 3/2014 Joao
2014/0095201 A1 4/2014 Farooq et al.
2014/0100861 A1 4/2014 Ledet
2014/0101172 A1 * 4/2014 Dua ....................... G06Q 10/10 707/750
2014/0142961 A1 5/2014 Luter et al.
2014/0222400 A1 8/2014 Coleman et al.
2014/0244300 A1 8/2014 Bess et al.
2014/0278556 A1 9/2014 Goltra et al.
2014/0278639 A1 9/2014 MacGillivray et al.
2014/0358576 A1 12/2014 Hoffman et al.
2014/0379374 A1 12/2014 Vinals
2015/0058039 A1 2/2015 Shiloh
2015/0120313 A1 4/2015 Cho et al.
2015/0161331 A1 * 6/2015 Oleynik ................. G16H 10/60 705/3
2015/0242568 A1 8/2015 Antony et al.
2015/0261794 A1 9/2015 Lehrian et al.
2015/0278393 A1 10/2015 Das et al.
2015/0339442 A1 * 11/2015 Oleynik ................. G16H 50/70 705/3
2015/0347590 A1 * 12/2015 Kamotsky ............. G06F 16/242 707/723
2015/0347688 A1 12/2015 Miller
2015/0379430 A1 * 12/2015 Dirac ..................... G06N 20/00 706/12
2016/0034642 A1 * 2/2016 Ehrhart .................. G16H 10/60 705/3

(56) References Cited

U.S. PATENT DOCUMENTS

| | | | |
|---|---|---|---|
| 2016/0048655 | A1 | 2/2016 | Maitra et al. |
| 2016/0125139 | A1 | 5/2016 | Higgs |
| 2016/0140204 | A1 | 5/2016 | Brown et al. |
| 2016/0147963 | A1 | 5/2016 | Bouhnik |
| 2016/0189321 | A1 | 6/2016 | Halpern et al. |
| 2016/0321406 | A1* | 11/2016 | Timmerman .......... G06Q 10/10 |
| 2016/0366010 | A1 | 12/2016 | Hamber et al. |
| 2017/0061093 | A1 | 3/2017 | Amarasingham et al. |
| 2017/0083547 | A1 | 3/2017 | Tonkin et al. |
| 2017/0161439 | A1 | 6/2017 | Raduchel et al. |
| 2017/0250973 | A1 | 8/2017 | Kimura |
| 2017/0262586 | A1* | 9/2017 | Bess ........................ G16Z 99/00 |
| 2017/0286600 | A1 | 10/2017 | Hasan et al. |
| 2017/0286621 | A1 | 10/2017 | Cox et al. |
| 2018/0005332 | A1 | 1/2018 | Testa et al. |
| 2018/0011921 | A1 | 1/2018 | Barclay |
| 2018/0060537 | A1 | 3/2018 | Tiwari et al. |
| 2018/0068089 | A1 | 3/2018 | Hu et al. |
| 2018/0308569 | A1 | 10/2018 | Luellen |
| 2019/0034475 | A1 | 1/2019 | Parikh et al. |
| 2019/0206531 | A1 | 7/2019 | Vandersluis |
| 2019/0279749 | A1* | 9/2019 | Wu ................... G06F 16/24578 |
| 2019/0286620 | A1 | 9/2019 | Al-Haimi et al. |
| 2019/0327311 | A1 | 10/2019 | Khassanov et al. |
| 2019/0349755 | A1 | 11/2019 | Maia et al. |
| 2019/0381005 | A1 | 12/2019 | Prybolsky et al. |
| 2019/0385710 | A1 | 12/2019 | Prybolsky et al. |
| 2020/0279622 | A1 | 9/2020 | Heywood et al. |
| 2020/0294677 | A1 | 9/2020 | Godinho et al. |
| 2020/0329982 | A1 | 10/2020 | Hengstmann et al. |
| 2021/0057071 | A1 | 2/2021 | Barber et al. |
| 2021/0090694 | A1* | 3/2021 | Colley ................... G16B 30/00 |
| 2021/0216506 | A1* | 7/2021 | Robinson ............ G06F 16/1748 |
| 2021/0225526 | A1 | 7/2021 | Viswanathan et al. |
| 2021/0240694 | A1 | 8/2021 | Mortensen et al. |
| 2021/0249139 | A1 | 8/2021 | Thakore et al. |
| 2021/0319558 | A1 | 10/2021 | Min et al. |
| 2021/0327553 | A1 | 10/2021 | Lee et al. |
| 2021/0357378 | A1* | 11/2021 | Urdiales ............... G06F 16/215 |
| 2022/0215948 | A1 | 7/2022 | Bardot |
| 2022/0415467 | A1 | 12/2022 | Shin et al. |

OTHER PUBLICATIONS

Oracle, “Oracle Argus Safety—User Guide” Oct. 2020, Release 8.2.2, 206 pages printed (Year: 2020).

Oracle Argus Safety, User’s Guide, Release 8.1, E70262-01, Sep. 2016.

Beumer, Michael “Load File Mapper Makes Importing Data Even Easier”, Jan. 2021 (based on Google Search date and page source tags), 7 pages retrieved from https://www.nextpoint.com/ediscovery-blog/improved-import-experience-2/. (Year: 2021).

* cited by examiner

SYSTEMS AND METHODS FOR ANALYZING ADVERSE EVENTS OF A SOURCE FILE AND ARRANGING THE ADVERSE EVENTS ON A USER INTERFACE

CROSS-REFERENCE TO RELATED APPLICATIONS

This application is a Continuation-In-Part of U.S. Pat. No. 11,907,305, filed Jul. 30, 2021 and issued Feb. 20, 2024, which claims priority to U.S. Provisional Patent Application No. 63/220,227, filed Jul. 9, 2021, both of which are incorporated herein by reference.

TECHNICAL FIELD

The present disclosure relates to systems and methods for analyzing adverse events of a source file and arranging the adverse events on a user interface as well as the field of Pharmacovigilance.

BACKGROUND

Researchers, scientists, industry players, academics, government regulators, and other stakeholders are increasingly in need of adverse event information that is accessible, easy to interpret, analyze, and/or visualize as well as that can be used to easily generate related cases.

SUMMARY

One embodiment relates to a method for generating a first case in an adverse event processing system, wherein the adverse event processing system includes a provider computing system, and a user computing device connected by a secure network. The provider computing system includes a database. The method includes receiving adverse event information associated with an adverse event. The adverse event information includes reporter information, patient information, medical product information associated with multiple medical products, and a type of the adverse event. The method further includes generating case information of the first case including the adverse event information and a medical product rank for each medical product of the multiple medical products associated with the medical product information. The method further includes selecting a second case which is a potential duplicate of the first case from the database based on the case information of the first case at least partially matching case information of the second case. The method further includes providing the case information of the first case and the second case to the user computing device to be displayed on a user interface. The user interface displays the case information of the first case adjacent to the case information of the second case and includes a button selectable to indicate the first case is not a duplicate of the second case. The method further includes generating, in response to receiving an indication of a selection of the button, the first case including the case information of the first case.

Another embodiment relates to a method for generating a first case in an adverse event processing system. The adverse event processing system includes a provider computing system, and a user computing device connected by a secure network. The method includes receiving adverse event information associated with an adverse event. The adverse event information includes reporter information, patient information, medical product information associated with multiple medical products, and a type of the adverse event. The method further includes generating case information of the first case including the adverse event information and a medical product rank for each medical product of the multiple medical products associated with the medical product information. The method further includes receiving a request to generate the first case from the user computing device. The method further includes selecting, in response to receiving the request, multiple potential duplicate cases which are each a potential duplicate of the first case from the database based on the case information of the first case at least partially matching case information of each potential duplicate case of the multiple potential duplicate cases. The method further includes categorizing each potential duplicate case of the multiple potential duplicate cases as a first category or a second category based on the case information of the first case and the case information of the potential duplicate case of the multiple potential duplicate cases. The method further includes receiving a type of the case from the user computing device and generating the first case including the case information of the first case based on the type of the first case.

This summary is illustrative only and is not intended to be in any way limiting. Other aspects, inventive features, and advantages of the devices or processes described herein will become apparent in the detailed description set forth herein, taken in conjunction with the accompanying FIGURES, wherein like reference numerals refer to like elements.

DETAILED DESCRIPTION

Figure 1:
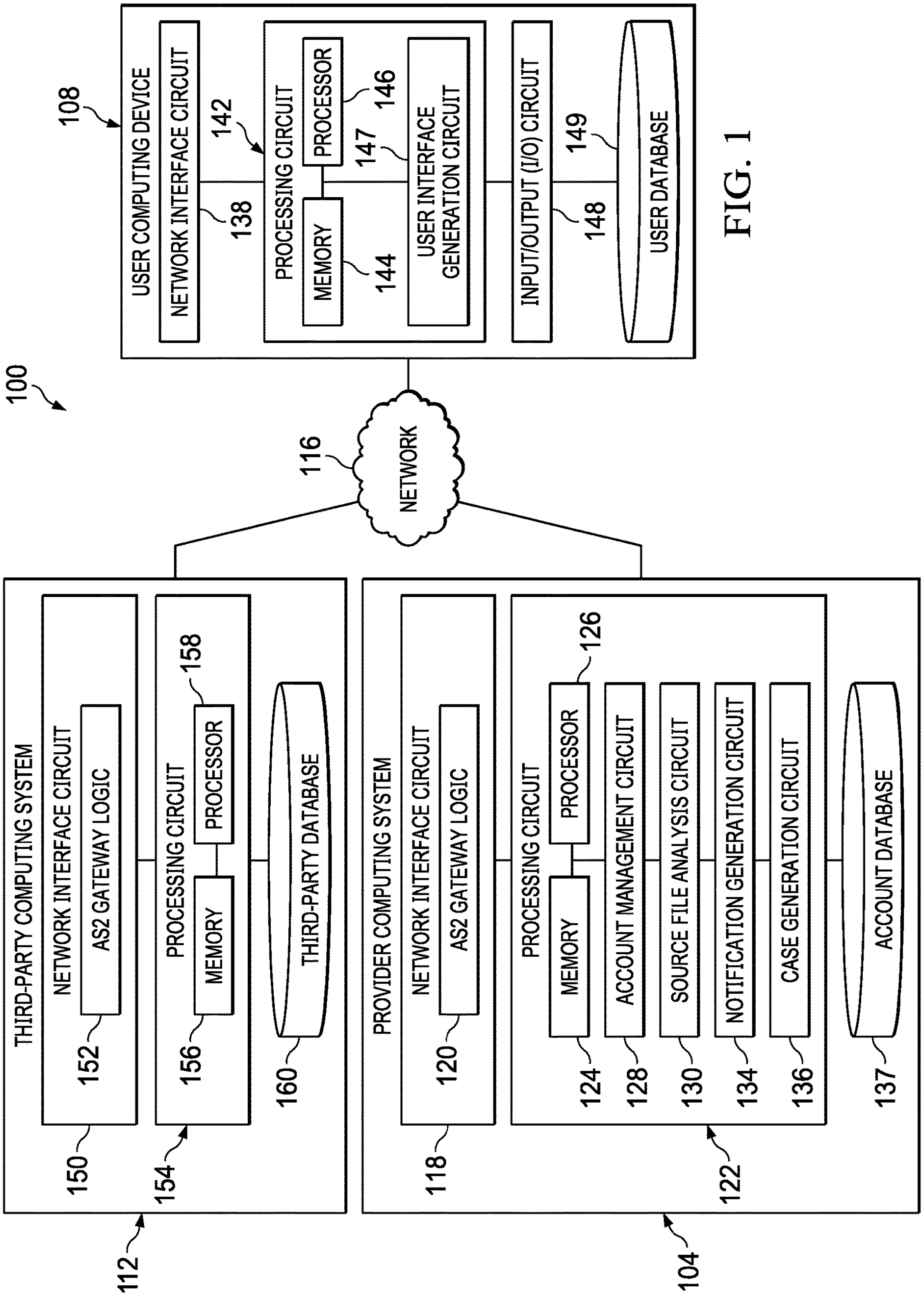
FIG. 1 is a component diagram of an adverse event analyzation and arrangement system, according to an example embodiment.

Referring generally to the figures, systems and methods for analyzing and arranging adverse events as well as generating related cases are disclosed. The systems and methods described herein provide for enhanced intake and analyzation of adverse events as well as generation of related Individual Case Safety Reports (ICSRs) by utilizing a wide variety of user data and account information such as stored user medial product information and stored user study information. For example, because the systems and methods described herein can utilize user data stored in a point-in time database in combination with information received on a source file, medical product and study information can be automatically populated in the ICSRs, which reduces the amount of memory usage as the medical product and study information does not need to be duplicated in multiple places and instead can be stored in one, shared, area. Further, because the medical product and study information can be automatically populated in the ICSR, the systems and methods described herein use less processing power than conventional systems as the user does not have to perform manual data entry multiple times and instead the medical product and study information only needs to be imported a single time.

The systems and methods described herein provide for an improved user interface by arranging the generated cases and the case information (e.g., case contacts or physicians, medical products, and medical events) on the user interface based on a determined rank. In conventional systems, a user typically has to parse an E2B XML file for adverse event information, determine the case information, and manually arrange the case information of the ICSR. In comparison and as will be further described herein, the present systems and methods may arrange the case information based on a determined rank for each piece of case information. In one example, multiple medical events may be arranged on the user interface based on the severity of the medical event such that the most severe medical event (e.g., cardiac arrest) is listed proximate the top of the user interface and the least severe medical event is listed proximate the bottom of the user interface. By doing so, the systems and methods described herein arrange the case information based on the pertinence and importance of the case information and provide an improved user interface for displaying case information. This arrangement provides the user with the important case information proximate the top of the user interface (i.e., where the user typically first looks), providing for a quick assessment of each piece of case information.

Moreover, the systems and methods described herein further provide for improved data storage as well as ICSR formatting. For example, because the case information (such as ranking and priority information) is generated automatically based on the adverse event information and stored user information, the associated case information is stored in an improved format. For example, because the case is assigned a priority based on the severity of the adverse event, the case is quickly assigned to other users and tasks associated with the case are better organized. In this regard, a case with a high priority will typically appear at a higher place (e.g., with a shortened timeline) and in more places than a case with a lower priority and be more accessible and reviewed faster.

Additionally, the systems and methods described herein provide for improved case duplication detection, and thereby help and improve the pharmacovigilance industry by more accurately tracking, capturing, and preventing the reporting of duplicate cases. For example, by automatically searching for and determining/selecting potential duplicate cases in response to receiving a request to generate a case, the present systems detect duplicate cases at a convenient time for the user (e.g., when they are in the process of generating the case), thereby providing an automatic check on duplicate cases that is not available in typical case processing and generation systems. Further, because the systems and methods described herein display the potential duplicate cases on a user interface directly after receiving the request to generate the case and in response to determining the potential duplicate cases, the present systems provide the user with an additional overview and inspection of the current case and potential duplicate cases that is not available in typical case processing and generation systems, which allows for quicker and more efficient duplicate case detection and management.

Likewise, because the present systems and methods rank the potential duplicate cases (e.g., as a first rank or as a second rank) based on the match between the case to be generated and the respective duplicate case and then arrange the potential duplicate cases on the user interface based on the rank, the present systems provide the user with an improved overview of the potential duplicate cases. Further, because the present and systems and methods then analyze and compare (e.g., via visual indications (e.g., colors, shapes, etc.)) a selected potential duplicate case and the case to be generated on a field-by-field and in a line-by-line manner, the present systems and methods further provide an easy-to-comprehend comparison and analysis of the differences and similarities between the case to be generated and the selected potential duplicate case, which allows the user to quickly analyze the two cases and make a decision on whether the potential duplicate is a duplicate, is a related case, or is not a duplicate.

Moreover, because the present systems and methods search for potential duplicate cases based on matching adverse events, reporters, and/or medical products, regardless of rank, the present systems and methods provide for a more accurate and effective searching methodology and a technical improvement to case duplication searching systems overall. For example, because the present systems and methods determine cases are potential duplicate cases based on the adverse events, the reporters, and/or the medical products of the potential duplicate cases and the case to be generated without taking into consideration the respective ranking of each, the present systems and methods more effectively find and determine duplicate cases than typical systems. For instance, a duplicate case may have an adverse event (e.g., "rash") with a rank "2," and the case to be generated may have an adverse event (e.g., "rash") with a rank "1" (e.g., the rash is the primary adverse event of the case). As a result, because the present systems and methods determine potential duplicate cases based on matches between the adverse events, reporters, and/or medical products, regardless of the rank assigned to each, the duplicate case described above would be detected by the systems and methods described herein.

As used herein, the term "event," "medical event," or "adverse event" can include any untoward medical occurrence which happens to either a patient or a subject in a clinical investigation or during regular use of a medical product that has been given to that person. For example, the "event," "medical event," or "adverse event" may encompass any signs which are unfavorable and unexpected for the patient or subject, including any abnormal laboratory findings such as a high blood pressure, a rapid heart rate, etc. The "event," "medical event," or "adverse event" could be symptoms, or a disease temporally associated with the use of a medical product and does not have to have been previously associated with that product. The term "event," "medical event," or "adverse event" can further encompass adverse reactions and serious adverse events such as death, life-threatening adverse experiences, inpatient hospitalization, congenital birth defects, disabilities, etc. Further, each "event," "medical event," or "adverse event" may be defined by the Medical Dictionary for Regulatory Activities (MedDRA) and associated with a specific MedDRA code. Moreover, "event information" "medical event information" "adverse event information" "event data" "medical event data" or "adverse event data" can include information associated with the event such as the date of onset of the event, the date of cessation of the event, the type of event, the dictionary term, the dictionary code (e.g., MedDRA code), event comments, the outcome of the event, the location of the event (e.g., country where the event occurred), the event duration, patient data for a patient who endured or to which the event occurred, medical products that the patient consumed and/or dosages for the consumed medical products, the event rank, event contacts, the event type, and any associated event documents.

Additionally, as used herein the terms "information" and "data" may be used interchangeably such that one may be substituted for the other and vice versa.

As used herein, the term "case" or "case dataset" can include an Individual Case Safety Report (ICSR) as defined by the standard ISO/HL7 27953 of the International Standards Organization (ISO) as well as any past or future standards governing ICSRs of the ISO, the Food and Drug Administration (FDA), the European Medicines Agency (EMA), or other national health agencies governing ICSRs. Moreover, "case information" "case data" or "case dataset" can include information associated with or included in the case such as adverse event data, case contact data, case priority data, case seriousness data, case documents, medical product registrations, patient data, and other data associated with a case as defined by the standard ISO/HL7 27953 as well as any past or future standards governing ICSRs of the ISO, the Food and Drug Administration (FDA), the European Medicines Agency (EMA), or other national health agencies governing ICSRs.

Referring now to FIG. 1, a system 100 for processing an adverse event and generating a related case is shown, according to an example embodiment. The system 100 includes a provider computing system 104, a user computing device 108, and a third-party computing system 112 connected by a secure network (e.g., a network 116).

The network 116 communicably and operably couples the provider computing system 104, the user computing device 108, and the third-party computing system 112 such that communicable and operable computing may be provided between the provider computing system 104, the user computing device 108, and the third-party computing system 112 over the network 116. In various embodiments, the network 116 includes may be any combination of a local area network (LAN), an intranet, the Internet, or any other suitable communications network, directly or through another interface.

The provider computing system 104 may be operated and managed by a provider (e.g., a software as a service (SaaS) provider, a cloud services provider, a software provider, a service provider, etc.) and may include a computer system (e.g., one or more servers (e.g., a cloud computing server) each with one or more processing circuits). In some embodiments, the provider computing system 104 may act as a host and provide an application (e.g., a web-based application, a mobile application, etc.) to the user computing device 108 over the network 116 in response to authenticating the user computing device 108. Further, the provider computing system 104 may include a network interface circuit 118, a processing circuit 122, and an account database 137. In some embodiments, the provider computing system 104 may include an input/output circuit (e.g., similar to (e.g., the same as) an input/output circuit 148 as will described further herein).

The network interface circuit 118 is structured to establish connections with the user computing device 108 and the third-party computing system 112 by way of the network 116. The network interface circuit 118 includes program logic (e.g., AS2 Gateway Logic 120) and/or hardware-based components that connect the provider computing system 104 to the network 116. For example, the network interface circuit 118 may include any combination of a wireless network transceiver (e.g., a cellular modem, a broadband modem, a Bluetooth transceiver, a Wi-Fi transceiver, a Li-Fi transceiver, etc.) and/or a wired network transceiver (e.g., an Ethernet transceiver). In some embodiments, the network interface circuit 118 includes the hardware and machine-readable media structured to support communication over multiple channels of data communication (e.g., wireless, Bluetooth, near-field communication (NFC). In some embodiments, the network interface circuit 118 includes cryptography logic and capabilities to establish a secure communications session.

The AS2 gateway logic 120 includes programmable instructions that facilitate communication (transmission and receipt) using the AS2 Gateway communication protocol (as specified in Request for Comment (RFC) 4130) over the network 116 via the network interface circuit 118. For example, using the AS2 gateway logic 120, the network interface 118 may transmit or receive files (e.g., the source file, a case, etc.) or other data to the third-party computing system 112 and/or the user computing device 108 using the AS2 Gateway protocol.

The processing circuit 122, as shown, comprises a memory 124, a processor 126, an account management circuit 128, a source file analysis circuit 130, a notification generation circuit 134, and a case generation circuit 136. The memory 124 includes one or more memory devices (e.g., RAM, NVRAM, ROM, flash memory, hard disk storage, etc.) that store data and/or computer code for facilitating the various processes described herein. That is, in operation and use, the memory 124 stores at least portions of instructions and data for execution by the processor 126 to control the processing circuit 122. The memory 124 may be or include tangible, non-transient volatile memory and/or non-volatile memory. The processor 126 may be implemented as a general-purpose processor, an application specific integrated circuit (ASIC), one or more field programmable gate array (FPGAs), a digital signal processor (DSP), a group of processing components or other suitable electronic processing components.

As described herein, the account management circuit 128 is structured to generate and manage, user accounts for various users (e.g., the user of the user computing device 108). For instance, the account management circuit 128 may be configured to generate an account and store account login credentials (e.g., a username and password) for the account within the account database 137 as well as provide the login credentials to the user computing device 108. Then, prior to providing the user computing device 108 access to account information (e.g., clinical study information, medical product information, account preferences, etc.) and functionality, the account management circuit 128 may require authentication of the user of the user computing device 108 via the account login credentials. Moreover, the account management circuit 128 may manage clinical study information (e.g., study name, study phase, study medical product of interest, study investigator, and the like) and medical product information (e.g., medical product type, medical product name, medical product dosage, medical product registration number, and the like) for the user. In operation, the user, via the user computing device 108, may provide clinical study information and medical product information to the account management circuit 128 of the processing circuit 122. The account management circuit 128 may then associate the user's clinical study information and medical product information with the account of the user and store the clinical study information and medical product information within the account database 137. In some embodiments, the account management circuit 128 is configured to encrypt and/or tokenize certain study information or medical product information prior to storing the study information or medical product information in the account database 137. For example, the study information may include private health information (PHI), as defined by the Health Insurance Portability and Accountability Act of 1996 (HIPAA) (or other laws that protect health information), and the account management circuit 128 may be configured to encrypt or tokenize the PHI. In another example, the study information may indicate the study is a blinded study (e.g., a double or single blinded study) and encrypt or tokenize the study information or medical product information for compliance.

The source file analysis circuit 130 is structured to receive, process, and analyze a source file for adverse event information relating to one or more adverse events. The source file may be any type of data file including PDF files, HTML files, ZIP files, CSV files, an email including attachments, XML files, etc. For example, the source file may be an E2B XML file (including defined attachments) as defined by the FDA. Further, the source file may include metadata that includes a field code or name for each field within the source file. In operation, the source file analysis circuit 130 may be configured to receive a source file (e.g., from the user computing device 108 or the third-party computing system 112) pertaining to one or more adverse events and including adverse event information for each adverse event. The source file analysis circuit 130 may then determine the version or type of data file (e.g., E2B (R2) or E2B (R3) of the source file and parse the source file for adverse event information pertaining to the adverse event. If the source file analysis circuit 130 determines the source file is missing one or more pieces of adverse event information (i.e., is not complete), the source file analysis circuit 130 may notify the user via the notification generation circuit 134. Next, the source file analysis circuit 130 may send the adverse event information to the case generation circuit 136 and the account management circuit 128. Moreover, the source file analysis circuit 130 may repeat the process recited herein for each adverse event within the source file.

The notification generation circuit 134 is structured to generate one or more notifications and provide them to the user computing device 108 or the third-party computing system 112. For example, the notification generation circuit 134 may generate a notification indicating that the source file is missing one or more pieces of adverse event information (i.e., is incomplete) and request the user of the user computing device 108 to provide the missing information. In another example, the notification generation circuit 134 may generate a notification indicating that the source file is not missing any adverse event information (i.e., is complete). Once the notification is generated, the notification generation circuit may interface with the network interface circuit 118 to provide the notifications to the correct recipient. Other notifications and capabilities of the notification generation circuit 134 will be discussed further herein.

The case generation circuit 136 may be structured to receive adverse event information (e.g., from a source file processed by the source file analysis circuit 130) as well as medical product information associated with the user (e.g., from the account database 137) and generate case information and a case including the case information. The case generation circuit 136 may further be configured to provide the case to the user computing device 108 or the third-party computing system 112 (e.g., via the AS2 Gateway Protocol) as well as interface with the account management circuit to associate the adverse event information and the case information with account information of the user. In some embodiments, the case generation circuit 136 may be structured or configured to determine potential duplicate cases associated with the case, rank each of the potential duplicate cases, and provide the potential duplicate cases to the user computing device 108 for display on a user interface. Other capabilities of the case generation circuit 136 will be discussed further herein.

As described herein, the account database 137 is a repository that receives, stores, and manages various account information (e.g., medical product information, login credentials, study information). To do so, the account database 137 can be structured according to various database types, such as, relational, hierarchical, network, flat, point-in time, and/or object relational. In operation, the account database 137 is configured to store account information in association with a specific user or specific users. Then, when requested, the account database 137 may provide the requested account information to a requesting party (e.g., the processing circuit 122). In some embodiments, multiple databases may take the place of a single account database and store/manage one or more pieces of the information that the account database is described herein as storing/managing. In one specific example, one or more of the user's case information, the case, the source file, medical product information, or study information may be stored in a point-in time database.

In some embodiments, each different data or information type (e.g., case information, preference information, medical product information, clinical study information, etc.) may be stored in, and the provider computing system 104 may include a separate database for each (not shown). For example, the provider computing system 104 may include a medical product database in which medical product information associated with a specific medical product is stored, a case database in which case information associated with a specific case is stored, a clinical study database in which clinical study information is stored, a preference database in which preference information associated with a specific account or user is stored, and so on for each type of information described herein. Each database may be the similar to or structured the same as the account database (e.g., relational, hierarchical, network, flat, point-in time, and/or object relational). In one example, the provider computing system 104 may include a case database (not shown) that the provider computing system 104 searches for potential duplicate cases of a specific case.

Still referring to FIG. 1, the user computing device 108 can be any type of computing device or system configured to run an application (e.g., a web-based application, a mobile application, etc.). For instance, the user computing device 108 can be one or more of a mobile phone, a tablet computer, a laptop computer, a smart watch, a server computer system, and any other internet-connected device that is capable of running an application. In operation, the user computing device 108 may download or connect to (e.g., via the network 116) the application of the provider computing system 104. Once downloaded or connected to the application of the provider computing system 104, the user computing device 108 may interface with the provider computing system 104 to exchange medical product information, account information, case information, etc. Further, the user computing device 108 is shown to include a network interface circuit 138, a processing circuit 142, the input/output (I/O) circuit 148, and a user database 149. While only a single user computing device 108 is shown, multiple computing devices can interface with the provider computing system 104 at one time in individual or shared computing environments. For example, as described herein, a source file may be received from a first user computing device and a notification indicating event information is incomplete may be provided to a second or third user computing device. In this regard, the user computing device 108 should be understood to encompass shared computing environments in which multiple users can be assigned a shared task.

The network interface circuit 138 is structured to establish connections with the provider computing system 104 and the third-party computing system 112 by way of the network 116. The network interface circuit 138 may be similar to the network interface circuit 118 and include program logic and/or hardware-based components that connect the user computing device 108 to the network 116. For example, the network interface circuit 138 may include any combination of a wireless network transceiver (e.g., a cellular modem, a broadband modem, a Bluetooth transceiver, a Wi-Fi transceiver, a Li-Fi transceiver, etc.) and/or a wired network transceiver (e.g., an Ethernet transceiver). In some embodiments, the network interface circuit 138 includes the hardware and machine-readable media structured to support communication over multiple channels of data communication (e.g., wireless, Bluetooth, near-field communication (NFC). In some embodiments, the network interface circuit 138 includes cryptography logic and capabilities to establish a secure communications session. Further, while the network interface circuit 138 is not shown to include AS2 Gateway logic (e.g., similar to the AS2 Gateway logic 120), the network interface circuit 138 may include AS2 Gateway logic and be capable of communication via the AS2 Gateway communication protocol.

The processing circuit 142, as shown, may comprise a memory 144, a processor 146, and a user interface generation circuit 147. The memory 144 includes one or more memory devices (e.g., RAM, NVRAM, ROM, flash memory, hard disk storage, etc.) that store data and/or computer code for facilitating the various processes described herein. That is, in operation and use, the memory 144 stores at least portions of instructions and data for execution by the processor 146 to control the processing circuit 142. The memory 144 may be or include tangible, non-transient volatile memory and/or non-volatile memory. The processor 146 may be implemented as a general-purpose processor, an application specific integrated circuit (ASIC), one or more field programmable gate array (FPGAs), a digital signal processor (DSP), a group of processing components or other suitable electronic processing components.

The user interface generation circuit 147 may be configured to receive a user interface (e.g., a web interface in an HTML file and related files, a downloaded graphical user interface, etc.) from the provider computing system 104 and render or generate the user interface on the user computing device 108 via the I/O circuit 148. In this way, the provider computing system 104 may generate one or more user interfaces (e.g., the user interface and pages shown and described herein) and provide the one or more user interfaces to the user interface generation circuit 147 to be rendered on the user computing device 108 (e.g., on a display of the I/O circuit 148 of the user device 108). Further functionality of the user interface generation circuit 147 as well as example user interfaces will be described further herein.

The I/O circuit 148 is structured to receive communications form and provide communications to the user of the user computing device 108 (e.g., the user). In this regard, the I/O circuit 148 is structured to exchange data with the processing circuit 142 to provide output to the user and to receive input from the user. As a result, the I/O circuit 148 may include a display that may be manipulated by the application. In some embodiments, the I/O circuit 148 may also include a keyboard, a mouse, a joystick, a touch screen, touch areas, soft keys, a microphone, a speaker, a vibration mechanism, a sensor, a RFID scanner, or other input/output mechanisms.

The user database 149 is a repository that receives, stores, and manages various information of the user (e.g., medical product information, login credentials, study information, and source files). To do so, the user database 149 can be structured according to various database types, such as, relational, hierarchical, network, flat, point-in time, and/or object relational. In operation, the user database 149 is configured to store information of the user, and, when requested, the user database 149 may provide the requested account information to a requesting party (e.g., the processing circuit 142). In one example, the user of the user computing device 108 may store and retrieve a source file in the user database 149 to be provided to the provider computing system 104 over the network 116.

Still referring to FIG. 1, the third-party computing system 112 is managed by a third-party (e.g., the FDA, the EHA, Health Canada) and can be any type of computing device or system configured to communicate with the provider computing system 104 or the user computing device 108 over the network 116. For instance, the third-party computing system 112 can be a server computer system, a gateway, a laptop computer a desktop computer, and any other internet-connected device that can communicate over the network 116. For example, the third-party computing system 112 may be the Electronics Submission Gateway (ESG) of the FDA through which one or more E2B XML files may be received from or provided to. In operation, the third-party computing system 112 may communicate with the provider computing system 104 or the user computing device 112 to send and/or receive one or more source files associated with adverse events (e.g., E2B files). Further, the third-party computing system 112 is shown to include a network interface circuit 150, a processing circuit 154, and a third-party database 160.

The network interface circuit 150 is structured to establish connections with the provider computing system 104 and the user computing device 108 by way of the network 116. The network interface circuit 150 may be similar to the network interface circuit 118 and includes program logic (e.g., AS2 Gateway Logic 152) and/or hardware-based components that connect the third-party computing system 112 to the network 116. For example, the network interface circuit 150 may include any combination of a wireless network transceiver (e.g., a cellular modem, a broadband modem, a Bluetooth transceiver, a Wi-Fi transceiver, a Li-Fi transceiver, etc.) and/or a wired network transceiver (e.g., an Ethernet transceiver). In some embodiments, the network interface circuit 150 includes the hardware and machine-readable media structured to support communication over multiple channels of data communication (e.g., wireless, Bluetooth, near-field communication (NFC). In some embodiments, the network interface circuit 150 includes cryptography logic and capabilities to establish a secure communications session.

The AS2 gateway logic 152 may be similar to the AS2 gateway logic 120 and includes programmable instructions that facilitate communication (transmission and receipt) using the AS2 Gateway communication protocol (as specified in Request for Comment (RFC) 4130) over the network 116 via the network interface circuit 150. For example, using the AS2 gateway logic 152, the network interface 150 may transmit or receive files (e.g., the source file, a case, etc.) or other data to the provider computing system 104 and/or the user computing device 108 using the AS2 Gateway protocol.

The processing circuit 154, as shown, may include a memory 156 and a processor 158. The memory 156 includes one or more memory devices (e.g., RAM, NVRAM, ROM, flash memory, hard disk storage, etc.) that store data and/or computer code for facilitating the various processes described herein. That is, in operation and use, the memory 156 stores at least portions of instructions and data for execution by the processor 158 to control the processing circuit 154. The memory 156 may be or include tangible, non-transient volatile memory and/or non-volatile memory. The processor 158 may be implemented as a general-purpose processor, an application specific integrated circuit (ASIC), one or more field programmable gate array (FPGAs), a digital signal processor (DSP), a group of processing components or other suitable electronic processing components.

The third-party database 160 is a repository that receives, stores, and manages various information of the third-party or the user (e.g., medical product information, study information, and source files). To do so, the third-party database 160 can be structured according to various database types, such as, relational, hierarchical, network, flat, point-in time, and/or object relational. In operation, the third-party database 160 is configured to store information of the third-party or the user, and, when requested, the third-party database 160 may provide the requested account information to a requesting party (e.g., the processing circuit 154). In one example, the third-party computing device 112 may store and retrieve a source file in the third-party database 160 to be provided to the provider computing system 104 over the network 116.

Figure 2:
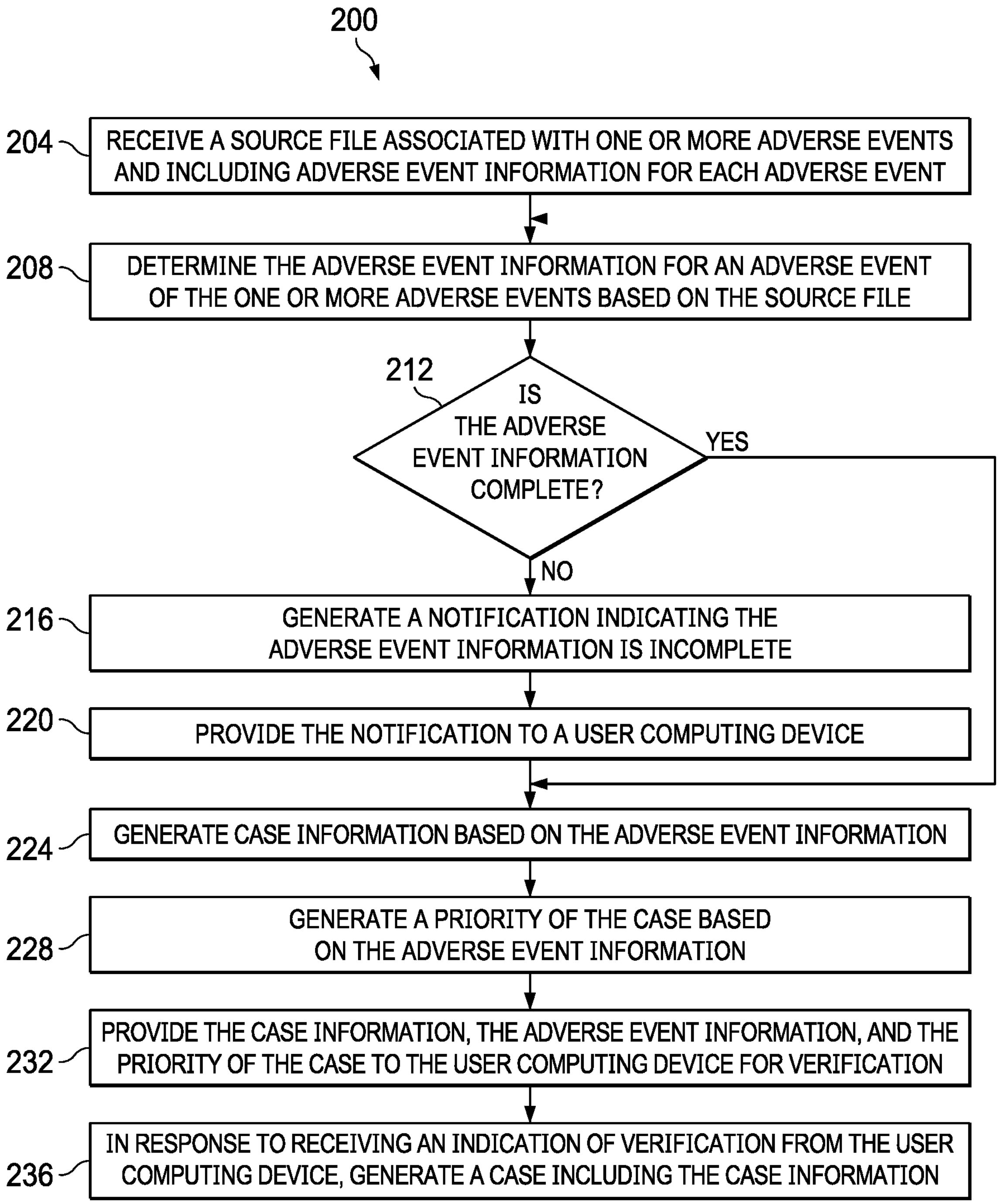
FIG. 2 is a flow diagram of a method for analyzing an adverse event of a source file and generating a related case, according to an example embodiment.

Referring now to FIG. 2, a method 200 of analyzing an adverse event of a source file and generating a related case is shown, according to an example embodiment. Method 200 can be carried out by the system of FIG. 1. More particularly, the method 200 can be carried out by the processing circuit 122 of the provider computing system 104 and through communication with the user computing device 108 and the third-party computing system 112.

Method 200 commences at step 204 at which a source file associated with one or more adverse events is received by the provider computing system 104. The source file may include adverse event information for each adverse event. In some embodiments, the source file may be received from one or more of an authenticated (or not authenticated) user of the user computing device 108 or from the third-party computing device 112. In some embodiments, the source file may be an E2B XML file received via an AS2 Gateway communication from the user computing device 108 or the third-party computing device 112. In other embodiments, the source file may be received from a third-party computing device (e.g., the third-party computing device 112) via an application programming interface (API) of the provider computing system 104. By using the API of the provider computing system 104, the third-party associated with the third-party computing device 112 may be able to autonomously send the source file to the provider computing system 104.

In some embodiments, at or before step 204, the provider computing system 104 receives user account information from at least one of the account database 137 or the user computing device 108. As described herein, account information may include login information associated with the user, medical product information associated with the user, study information associated with the user, and any user preferences (i.e., any preferences associated with the user). In some embodiments, the user may set preferences such as required adverse event information (i.e., adverse event information required for the adverse event information to be considered complete), required medical product information (i.e., medical product information required for the medical product information to be considered complete), user permissions (i.e., which other users may access the user's medical product information, notifications, etc.), and the like.

Once the provider computing system 104 has received the source file, the method 200 proceeds to step 208 at which the provider computing system 104 determines the adverse event information for one adverse event of the one or more adverse events based on the source file. In some embodiments, the provider computing system 104, at step 208, may determine the adverse event information for each adverse event of the one or more adverse events contained within the source file. As described herein, the adverse event information can include information relating to the event such as the type of event, the event code, event contact(s), patient information for a patient who endured or to which the event occurred (e.g., PHI), and medical products that the patient consumed and/or dosages for the consumed medical products.

In some embodiments, at or before step 208, the provider computing system 104 may determine the type of the source file. For example, at step 208, the provider computing system 104 may first determine the type of the source file (e.g., E2B (R3) XML file, CSV file, PDF file, etc.) and then determine the adverse event information for the adverse event based on the source file and the type of the source file. Likewise, at or before step 208, the provider computing system 104 may determine the sender or origin of the source file. For example, at step 208, the provider computing system 104 may first determine the origin of the source file (e.g., the third-party computing system 112, the user computing device 108, the United States (the FDA), Canada (Health Canada), Europe (EHA), etc.) and then determine the adverse event information for the adverse event based on the source file, the type of source file, and/or the origin or sender of the source file. Because different health agencies (e.g., the FDA, the ESA) can have different adverse event reporting standards, different countries can include different adverse event information within source files.

Once the provider computing system 104 has determined the adverse event information for the adverse event contained within the source file, the method 200 proceeds to step 212 at which the provider computing system 104 determines if the adverse event information is complete based on the required adverse event information. In some embodiments, the adverse event information may be considered complete if the adverse event information includes all adverse information required (i.e., origin or location required adverse event information) by the respective health agency (e.g., the FDA, the EHA, etc.). In other embodiments, the adverse event information may be considered complete if the adverse event information includes all the fields or field codes specified in the source file. For example, the source file may be an E2B (R3) XML file that includes field codes for the adverse event information including one or more patient information field codes, one or more medical product information field codes, study information field codes, a type of the adverse event field code, and a country field code. Then, based on the type of the source file (e.g., E2B (R3) XML file) and the field codes of the XML file, the provider computing system 104 may determine that the adverse event information is complete because it includes each of the patient information associated with the adverse event, the medical product information associated with the adverse event, the study information associated with the adverse event, the type of adverse event, and the country in which the adverse event occurred. In another example, the provider computing system 104 may determine that the adverse event information is incomplete because it does not include one or more of the patient information associated with the adverse event, the medical product information associated with the adverse event, the study information associated with the adverse event, the type of adverse event, or the country in which the adverse event occurred.

In some embodiments, the required adverse event information and the field codes may also specify the format of each piece of the required adverse event information. For example, the required adverse event information and the field codes of the source file may include patient information associated with the adverse event and specify that the patient information much include a first name, a last name, and patient contact information (e.g., a phone number, an email, etc.). In another example, the required adverse event information may include medical product information and specify that at least one piece of the medical product information match a medical product stored by the user in the account database 137. In a final example, the required adverse event information may include the country in which the adverse event occurred and specify that the full country name be listed and an actual country (e.g., “Sweden” not “SE” or “Swede”).

If, at step 212, the provider computing system 104 determines that the adverse event information is incomplete (i.e., not included or in the incorrect format), the method 200 proceeds to step 216 at which the provider computing system 104 generates a notification indicating the adverse event information is incomplete. In some embodiments, the notification may specify which portions of the required adverse event information are missing or incomplete. For example, the notification may indicate that the adverse event information does not include medical product information that matches a medical product stored by the user in the account database 137. In another example, the notification may indicate that the adverse event information does not include a country in which the adverse event occurred and does not include the correct format for the adverse event type (e.g., does not include a MedDRA code, etc.).

Once the provider computing system 104 has generated the notification indicating that the adverse event information is incomplete, the method 200 may proceed to step 220 at which the notification is provided to the user computing device 108. In some embodiments, the notification may be provided to the user computing device 108 and displayed on a user interface to be provided to the user. Further, in some embodiments, the notification may also be provided to the user computing device 108 via an email. In this regard, the user of the user computing device 108 may receive two notifications or two copies of the notification, one on the user interface displayed on the user computing device 108 as described herein and another via the user’s email address. The notification may be displayed and indicate which portions of the adverse event information are missing or in the incorrect format and request correction. In some embodiments, the provider computing system 104 may not proceed from step 220 until the user has corrected the missing adverse event information by sending or correcting the adverse event information via the user computing device 108 (i.e., until the provider computing system 104 has received the missing or corrected adverse event information from the user computing device 108). In other embodiments, the provider computing system 104 may proceed form step 220 once the notification has been provided to the user computing device 108.

If, at step 212, the adverse event information is determined to be complete, or after the provider computing system 104 has provided the notification to the user computing device 108 at step 220, the method 200 proceeds to step 224. At step 224, the provider computing system 104 generates case information based on the adverse event information. In some embodiments, the provider computing system 104 generates the case information based on the adverse event information and the missing or corrected adverse event information received from the user computing device 108. As described herein, the case information may include the adverse event information as well as other information pertaining to the ICSR such as the case contact and the case documents (e.g., the source file). In some embodiments, the provider computing system 104 may generate case information by transforming adverse event information that is in an incorrect format into a correct format (e.g., “SE” to “Sweden”). In this regard, the case information may be generated to include the corrected adverse event information, the missing adverse event information, and the correct adverse event information received in the source file. In some embodiments, the provider computing system 104, before or at step 224, may request and receive the missing adverse event information from the user computing device 108 to then be added to the case information.

Further, at or before step 224, the provider computing system 104 may retrieve the medical product and/or study information of the user from the account database 137 and generate case information by matching adverse account information with the medical product and/or study information. For example, the adverse event information may indicate that the patient consumed Y Milliliters of a medical product X on Mar. 23, 2000. The provider computing system 104 may then search the account database 137 (or a separate account database (not shown)) for information pertaining to medical product X and return additional values and medical product information (e.g., dosage of medical product X, the chemical formula of medical product X, expected side effects of medical product X, a clinical study that medical product X is currently being studied in, a clinical study #, pertaining to medical product X, and the like) as previously provided by the user. This additional medical product information and study information may then be included in the case information. In another example, the adverse event information may indicate that the patient consumed medical products A, B, and C on Mar. 23, 2000. The provider computing system 104 may determine that the user has not provided any medical product information pertaining to medical products A and B but has provided medical product information pertaining to medical product C. Accordingly, the provider computing system 104 may retrieve the medical product information pertaining to medical product C as well as assign a ranking of one to the medical product C, while assigning a ranking of two or three to the medical products A and B. The ranking may then be used to list or sort the medical product information within the case (i.e., a ranking of one appears higher than a ranking of two, and so on) and on any user interfaces.

Once the provider computing system 104 has generated case information, the method 200 may proceed to step 228 at which the provider computing system 104 generates a priority of the case based on the adverse event information. The priority of the case may be used to determine the order in which the case appears for verification and processing as well as to assign a due date/time or timeframe (e.g., seven days from receipt of the source, a month from receipt of the source file, etc.) in which the case must be reported to one or more health agencies. As a result, the priority of the case may be generated based on the severity of the type or outcome of the adverse event (e.g., death, hospitalization, minor illness, etc.). In some embodiments, the priority of the case may be generated based on the user preferences. In other embodiments, the provider computing system 104 may generate the priority of the case based on the health agency to which the case must be reported and any applicable laws or health agency requirements.

Once the provider computing system 104 has generated and assigned the priority for the case, the method 200 proceeds to step 232 at which the provider computing system 104 provides the case information, the adverse event information, and the priority of the case to the user computing device 108 for verification. In some embodiments, the provider computing system 104 may also generate and provide a notification to the user computing device 108 indicating that verification of the case information and the priority is requested. In some embodiments, the case information, the adverse event information, and the priority of the case may be provided to the user computing device 108 and presented to the user via a user interface for verification and as will be discussed further herein. In some embodiments, the provider computing system 104 may not send the case information, the adverse event information, and the priority of the case to the user computing device 108, if any of the information is not complete (as defined by the user's preferences). For example, the user may indicate that the case information is to include a full name of the patient. Then, at step 232, if the patient's full name is not included in the case information, the provider computing system 104 may generate a notification indicating as such and not proceed to the next step until the patient's full name is received.

Once the user provides an indication of verification (e.g., via the user interface and the I/O circuit 148 of the user computing device 108), the method 200 proceeds to step 236. At step 236, the provider computing system 104 generates a case including the case information and the case priority, in response to receiving an indication of verification from the user computing device 108. Further, at or after step 236, the provider computing system 104 may store the case, in association with the user, in the account database 137. In some embodiments, the step 236 and generating a case are initiated by receiving an indication from the user (e.g., from the user computing device 108) to generate a case. Further, in some embodiments, the provider computing system 104 checks the case information, adverse event information, and source file against other cases stored in the account database 137. For example, the provider computing system 104 may return a list of cases to which the potential case may be a duplicate of or be related to and provide the list to the user computing device 108. In response to the user computing device 108 indicating that the potential case is not a duplicate, the user computing device 108 may then generate the case and store the case in the account database 137. Further duplicate searching features will be discussed further herein with regard to method 800.

In some embodiments, at or after step 236, the provider computing system 104 may be configured to provide the case to one or more of the user computing device 108 or the third-party computing system 112. In one example, the case may be stored in the form of an E2B XML file and provided to one or more of the user computing device 108 or the third-party computing system 112 via an AS2 Gateway communication. In some embodiments, the provider computing system 104 may provide the case based on the priority of the case (e.g., a case with priority of one is provided before a case with a priority of two). In other embodiments, the provider computing system 104 may receive an indication or request from the user computing device 108 to provide the case to the third-party computing system 112 and do so in response. In some embodiments, the provider computing system 104 may automatically provide the case based on the timeframe of the case. For example, if the case had a timeframe of seven days from receipt of the source file and it has been seven days from receipt of the source file, the provider computing system 104 may automatically provide the case to one or more of the user computing device 108 or the third-party computing system 112.

After step 236, the provider computing system 104 determines if the source file includes an unprocessed adverse event. As each source file may include multiple adverse events, the provider computing system 104 may determine that only a portion of the adverse events within the source file have been processed, analyzed, and included in a case. In some embodiments, instead of processing each adverse event at a time, the provider computing system 104 may process all the adverse events at one time. If the provider computing system 104 determines that the source file includes an unprocessed adverse event, the method 200 returns to step 208 and the unprocessed adverse event is processed. The method 200 is then repeated, from step 208, for each unprocessed adverse event within the source file.

Referring now to FIGS. 3-7, user interfaces shown to the user of the user computing device 108 during the method 200 and/or the method 800 are shown, according to example embodiments. As described herein, the user interfaces of FIGS. 3-7 may be one or more of web interfaces generated by the provider computing system 104 and rendered by the user computing device 108 as part of a web application or graphical user interfaces downloaded and generated by the user computing device 108 as part of a software application (e.g., mobile application, etc.). Further, the user interfaces shown on FIGS. 3-7 allow for communication between the user and the provider computing system 104 via the user computing device 108 (specifically via the I/O circuit 148). Through interaction with the various user interfaces, the user may provide user input, feedback, and other information requested by the provider computing system 104. In this regard, it should be understood that each interaction described herein by the user with the user interfaces of FIGS. 3-7 may be provided to the user computing device 108 and then transmitted to the provider computing system 104 and that each action described herein as occurring to or on the user computing device 108 (e.g., navigating to a certain page, generating a popup, etc.) may be performed by the provider computing system 104.

Figure 3:
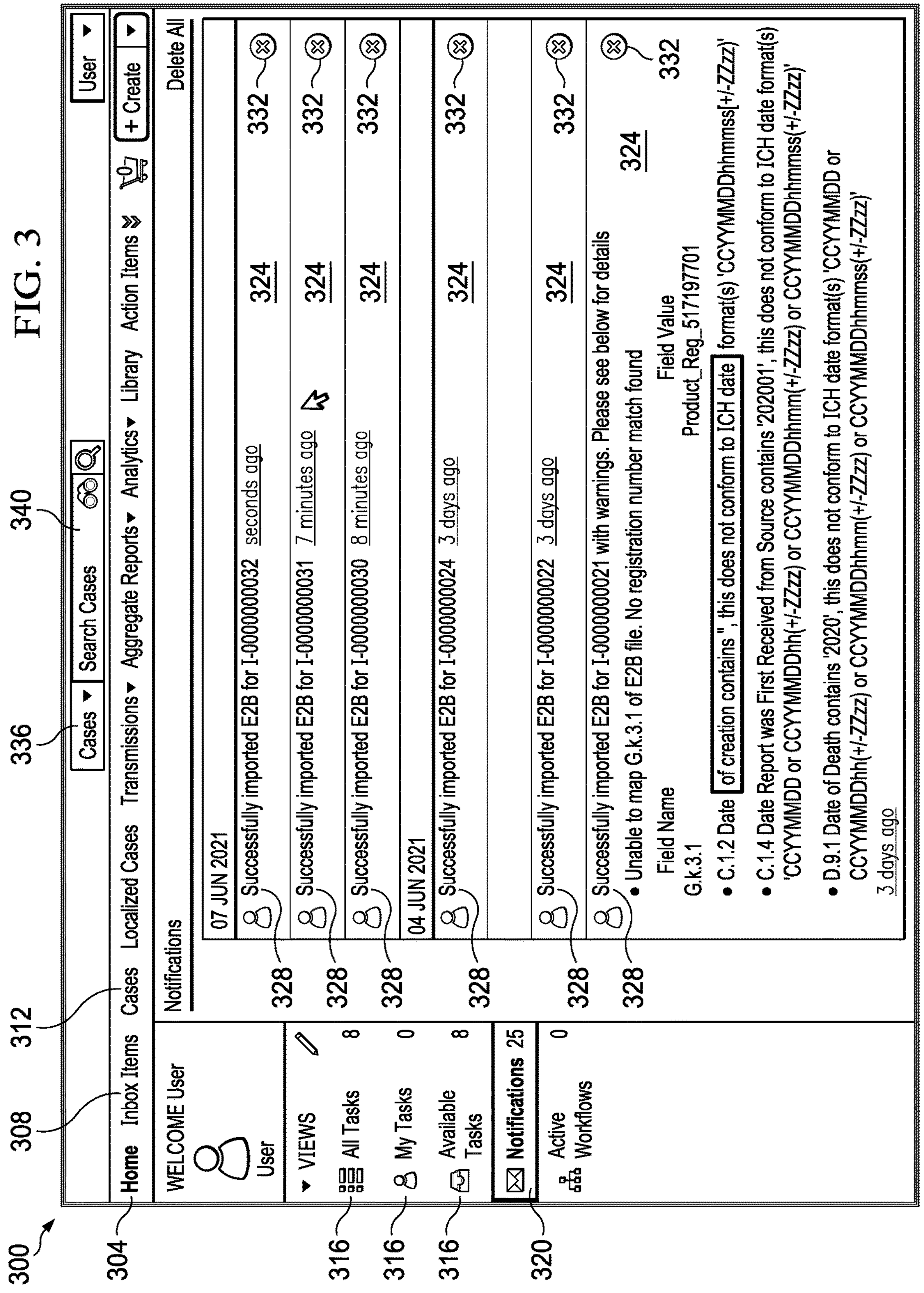
FIG. 3 is an illustration of some aspects of a user interface generated by the adverse event analyzation and arrangement system of FIG. 1 after generation of a notification, according to an example embodiment.

Referring now to FIG. 3, a home page 300, which can be displayed on a display of the I/O circuit 148 of the user computing device 108, is shown. In general, the home page 300 provides the user with an overview of their account as well as any notifications or tasks that the user is assigned. As shown, the home page 300 includes a home page button 304, an inbox items button 308, and a cases button 312. The home page button 300 is a selectable (clickable, pressable, etc.) button that navigates the user to the home page 300. In some embodiments, the home page button 300, when selected, navigates the user to a web page that displays the home page 300. Similarly, the inbox items button 308 and the cases button 312 are selectable buttons that navigate the user to an inbox items management page (not shown) and a cases management page (not shown), respectfully. While the inbox items management page and the cases management page are not shown, it should be understood that the inbox items management page generally shows and provides for management of inbox items (e.g., newly received source files, newly received adverse events from source files, etc.) that are associated with the user and the cases management page generally shows and provides for management of cases that are associated with the user. In some embodiments, the cases shown on the case management page are arranged based on the priority of each of the cases as will be described further herein. By arranging each case based on the priority of the case, the most pertinent cases are shown proximate the top of the case management page, where the user typically first looks, and the least pertinent cases are shown proximate the bottom of the case management page.

The home page 300 is further shown to include multiple task buttons 316 (e.g., "all tasks," "my tasks," and "available tasks") and a notifications button 320. The task buttons 316 are each selectable buttons that navigate the user to their available or managed tasks (e.g., review of cases, review of adverse events, etc.) on the home page 300. Similarly, the notifications button 320 is a selectable button that navigates the user to their available or managed notifications (e.g., as discussed with respect to the step 216) on the home page 300. As shown, the home page 300 is currently displaying multiple notifications 324 of the user.

As described herein, the provider computing system 104 may generate one or more notifications 324 and provide them to the user of the user computing device 108 via a user interface (e.g., via the home page 300) to indicate the status of inbox items and adverse events. As a result, the notifications 324 are shown to include a status 328 and a hide notification button 332. The status 328 may indicate the status of whatever the notification is indicating. In this example, the notifications 324 indicate the status 328 of the inbox items and their respective adverse event information. For example, the status 328 of the first notification 324 states "Successfully imported E2B for I-00000000032," which may indicate that a received source file included all the required adverse event information. In comparison, the status 328 of the last (bottom) notification 324 states "Successfully imported E2B for I-00000000000021 with warnings." "Unable to map G.k.3.1 of E2b FILE. No registration number match found," which may indicate that a received source file is missing required adverse event information (e.g., a registration number) or that the registration number is in an incorrect format. The status 328 may also include a time stamp (e.g., "seconds ago," "7 minutes ago") that indicates when the notification 324 was received. Further, in some embodiments, the inbox item name (e.g., "I-00000000032,") in the status 328 may be a selectable hyperlink that, when selected, navigates the user to the respective inbox item.

The hide notification button 332 of each notification 324 may be a selectable button that hides or deletes the notification 324. In some embodiments, the hide notification button 332 hides the respective notification 324 such that is it is considered viewed and/or processed (e.g., the number next to the notifications button 320 decreases by one) but is still available on the home page 300. In other embodiments, the hides notification button 332 deletes the respective notification 324 such that is it is considered viewed and/or processed (e.g., the number next to the notifications button 320 decreases by one) and is no longer available on the home page 300.

The home page 300 is further shown to include a search bar having a search type drop down box 336 and a search text field 340. Through use of the search bar, the user may indicate one or more types of information they would like to search for as well as a name or identifier of the information. For example, the user may select the drop down box 336 and indicate they are searching for "Cases" as well as type a case name (e.g., "First test case") into the search text field. The user may then hit the search button (magnifying glass button on the right) and be navigated to a search results page. Once the search button is selected, the provider computing system 104 may search the account database 137 for a case associated with the user and the name of the case entered by the user and return any results via the search results page. While not shown, the search results page may include details pertaining to any resulting search results.

In general, when a button is selected on the home page 300 and other user interfaces described herein, the button may become emphasized (e.g., highlighted, filled with color) or unclickable to indicate that the user is already viewing the associated information or page. For example, on FIG. 3, the home page button 300 (e.g., the term "Home") is highlighted orange to indicate that the user is currently viewing the home page 300. Likewise, the notifications button 320 is also colored orange to indicate that the user is currently viewing the user's notifications on the home page 300.

Referring now to FIGS. 4A-4G, an inbox item page 400, which can be displayed on a display of the I/O circuit 148 of the user computing device 108, is shown. In general, the inbox item page 400 provides the user with management (e.g., review, verification, revision, etc.) of an inbox item and shown/display the generated case information, the adverse event information, and the priority information for the case to the user (as described herein with respect to step 232). To get to the inbox item page 400, the user may navigate via the inbox items management page (e.g., by selecting the inbox item on the inbox items management page) or by selecting the selectable or hyperlinked inbox item name in the status 328 of a notification 324 on the home page 300.

The inbox item page 400 is shown to include a scroll bar 401, a case validity and source button 402, an edit button 403, a details button 404, an options button 405, a case contacts button 406, a patient button 410, a medical events button 412, a documents button 414, a workflow timeline button 416, and a settings button 418. Each of the case validity and source button 402, the edit button 403, the options button 405, the case contacts button 406, the patient button 410, and the medical events button 412 are selectable buttons that navigate the user on the inbox items page 400, navigate the user to another page, or provide the user with various functionality and will be described further herein. The scrollbar 401 is a selectable bar that allows the user to navigate the inbox items page 400 via a mouse, keyboard, trackpad, etc.

The documents button 414 is a selectable button that navigates (e.g., automatically scrolls the user and the inbox item page 400) to a documents section (not shown) of the inbox item page 400. The documents section may include information (e.g., a version) relating to as well as links of one or more documents associated with the inbox item such as the source document itself, a medical report, etc.

The workflow timelines button 416 is a selectable button that navigates (e.g., automatically scrolls the user and the inbox item page 400) to a workflow timeline section (not shown) of the inbox item page 400. The workflow timeline section may include information relating to one or more workflows (e.g., review, verification, promotion to a case, etc.) and tasks associated with the inbox item.

The settings button 418 is a selectable button that navigates (e.g., automatically scrolls the user and the inbox item page 400) to a settings section (not shown) of the inbox item page 400. The settings section may include information (e.g., a version) relating to the user's preferences (as received from the account database 137) such as the user's required adverse event information, other users who can access tasks, inbox items, and cases associated with the user, and other preferences or settings described herein.

The details button 404 is a selectable button that navigates (e.g., automatically scrolls the user and the inbox item page 400) to a details section 419 of the inbox item page 400. The details section 419 is shown to include a toggleable header 420, a priority field 421, multiple case information fields 422, and a source data viewer 424 that displays multiple pieces of related adverse event data from the source file. In general, the details section 419 displays and provides the user with high-level case information for management and review. Further, if the user has fully reviewed the details section 419, the toggleable header 420 is a selectable and toggleable button that shows or hides the details section 419. Therefore, by selecting the toggleable header 420, the user can hide the information and fields of the details section 419, or, when already hidden, show and display the information and fields of the details section 419.

The priority field 421 may display the generated case priority described herein for review and acceptance by the user. As shown, the priority field 421 may include a drop-down box with multiple selectable priorities (i.e., P1, P2, P3). In the embodiment shown, the case priority was generated as P1 as the adverse event resulted in death (see "Suggestion") and the priority field 421 was automatically populated with the respective priority. In other embodiments, the priority field 421 as well as any other fields described herein may be at least one of a text field, a date field, a checkbox field, a table, a lookup table, or other types of fields through which the user can interact, edit, and verify the respective field.

The case detail fields 422 are editable fields (e.g., text fields, date fields, etc.) that are automatically populated with the generated case information received from the provider computing system 104. The case detail fields 422 are automatically populated with the generated case information and provided to the user via the user computing device 108 for review, editing, and verification. While each specific case detail field 422 will not be covered in detail, it should be understood that case information as described herein can include the shown information of each case information field 422 (e.g., with respect to FIG. 4A, receipt date, report type, study, reporter's comments) as well as the other fields described herein.

The source data viewer 424 includes and displays the adverse event information (i.e., from the source file) that was used to generate the case information of the case detail fields 422 side by side with the case information of the case detail fields 422. Furthermore, the source data viewer 424 may include and display the field names or codes of the source file (e.g., "C1.4") proximate or directly adjacent to the adverse event information that was included in the respective field (e.g., "2015 Mar. 2"). Each field code may be determined by the provider computing system 104 based on metadata of the source file and be provided to the user computing device 108 in association with the adverse event information that was included in the field with the respective field code. As shown, the source data viewer 424 includes a plurality of adverse event information that is non-editable and allows for the user to quickly verify the generated case detail fields 422 were correctly generated. Further, by providing the source data viewer 424 side by side with the case detail fields 422, the inbox items page 400 provides for a user interface that quickly allows for verification, provides for enhanced information accuracy, and reduces case intake and generation time. For example, because the source data viewer is side by side with the case detail fields 422, the user can easily verify the generated case information and does not have to review the source document itself (e.g., an XML file), which can be slow and difficult to analyze. As a result, the case intake and generation process are shortened, saving on processing power that would be required to view the source document in combination with the case information. While each specific adverse event text of the source data viewer 424 will not be covered in detail, it should be understood that adverse event information as described herein can include the shown information of the source data 424 (e.g., with respect to FIG. 4A, receipt date, report type, reporter's comments, new info date, worldwide UID, study name, study number, etc.).

In some embodiments, one or more case detail fields 422 (e.g., "Study") will not be populated if the account database 137 does not include matching information (e.g., study information) as described herein. For example, the source data viewer 424 is shown as including a study information ABC-123. However, the case information of the case detail fields 422 is empty (e.g., not generated) which may be the result of the account database 137 not including study information matching ABC-123.

Through interaction with the priority field 421 and the case detail fields 422, the user may edit, add, or update the case information (i.e., by entering new text within the case detail fields 422). Once the user has entered new information or verified the information is correct, the user may select the selectable verify button 425. The verify button 425 may be configured to save the information within the case information fields 422 or the priority field 421 (i.e., to update and save the newly entered case information in place of the old case information). In some embodiments, selecting the verify button 425 may also provide an indication to the provider computing device 104 that the related case information is verified.

The case contacts button 406 is a selectable button that navigates (e.g., automatically scrolls the user and the inbox item page 400) to a case contacts section 426 of the inbox item page 400. The case contacts section 426 is shown to include a toggleable header 427 and one or more case contacts 428. Each case contact representation 428 may include a toggleable header 429, multiple case contact fields 430, and the source data viewer 424. In general, the case contacts section 426 displays and provides the user with case contact case information for each case contact representation 428 and for management and review. Further, if the user has fully reviewed the case contacts section 426 the toggleable header 420 is a selectable and toggleable button that shows or hides the case contacts section 426. Similarly, if the user has fully reviewed the case contact representation 428, the toggleable header 429 is a selectable and toggleable button that shows or hides information pertaining to the case contact representation 428.

The case contact fields 430 may be substantially the same as the case detail fields 422 and are editable fields (e.g., text fields, date fields, etc.) that are automatically populated with the generated case information received from the provider computing system 104. The case contact fields 430 are automatically populated with the generated case information (i.e., case contact case information) and provided to the user via the user computing device 108 for review, editing, and verification. The case contact fields 430 and the related case information is shown to include a rank field. The rank field may dictate the order in which the case contacts 428 are arranged on the inbox item page 400 and on the case itself (e.g., rank one is listed above rank two, which is listed above rank three, and so on). In some embodiments, the rank may be generated based on the type of the case contact within the adverse event information. For example, the case contact listed as the "reporter" may be assigned rank one. In other embodiments, the rank for each case contact representation 428 is assigned based on title (e.g., Dr. is ranked highest, etc.) or based on alphabetization of names.

Through interaction with the case contact fields 430, the user may edit, add, or update the case information (i.e., by entering new text within the case contact fields). Once the user has entered new information or verified the information is correct, the user may select the selectable verify button 425. Similarly, if the user would like to remove the case contact representation 428, the user may select the selectable delete button 432. The delete button 432 may remove and delete the case contact representation 428 and any case information pertaining to that case contact. Then, the case contact representation 428 ranked below the current case contact representation 428 (e.g., the rank two case contact representation 428) may become the rank one case contact representation 428 and so on.

The patient button 408 is a selectable button that navigates (e.g., automatically scrolls the user and the inbox item page 400) to a patient section 434 of the inbox item page 400. The patient section 434 is shown to include a toggleable header 436, multiple patient fields 438, and the source data viewer 424. In general, the patient section 434 displays and provides the user with patient information (e.g., the patient that experienced the adverse event) for management and review. Further, if the user has fully reviewed the patient section 434, the toggleable header 436 is a selectable and toggleable button that shows or hides the patient section 434.

The patient fields 438 may be substantially the same as the case detail fields 422 and are editable fields (e.g., text fields, date fields, etc.) that are automatically populated with the generated case information received from the provider computing system 104. The patient fields 438 are automatically populated with the generated case information (i.e., case patient information) and provided to the user via the user computing device 108 for review, editing, and verification. In some embodiments, the patient fields 438 (and the source data viewer 424) may include tokenized or encrypted information (e.g., such that the user cannot discern PHI from the patient fields 438). By doing so, the PHI of the patient may be protected from unauthorized users viewing said information. In other embodiments, only patient fields 438 that contain PHI are tokenized or encrypted. In some embodiments, the patient fields 438 (and the source data viewer 424) may include tokenized or encrypted information, if the user is not authorized to see the PHI of the patient. For example, the provider computing system 104 may determine, based on the user's account login credentials, the user is not authorized to see the PHI of the patient, and may encrypt or tokenize the respective case information prior to it being provided to the user computing device 108.

The products button 410 is a selectable button that navigates (e.g., automatically scrolls the user and the inbox item page 400) to a products section 439 of the inbox item page 400. The products section 439 is shown to include one or more products (e.g., medical products) representations 440. Each product representation 440 may include a toggleable header 442, multiple product fields 444, a dosage 445, and the source data viewer 424. In general, the products section 439 displays and provides the user with product information for each product representation 440 and for management and review. Further, if the user has fully reviewed the product, the toggleable header 442 is a selectable and toggleable button that shows or hides information pertaining to the product 440.

The product fields 444 may be substantially the same as the case detail fields 422 and are editable fields (e.g., text fields, date fields, etc.) that are automatically populated with the generated case information received from the provider computing system 104. The product fields 444 are automatically populated with the generated case information (i.e., case medical product information) and provided to the user via the user computing device 108 for review, editing, and verification. The product fields 444 and the related product information is shown to include a rank field. The rank field may dictate the order in which the products 440 are arranged on the inbox item page 400 and on the case itself (e.g., rank one is listed above rank two, which is listed above rank three, and so on). In some embodiments, the rank may be generated based on determining that the product (e.g., medical product) matches a product in the account database 137 associated with the user. For example, the product representation 440 that matches a product in the account database 137 may be ranked one. In other embodiments, the rank for each product representation 440 is assigned based on known side effects or based on alphabetization of names.

The dosage 445 is an additional section of fields that includes case information relating to a dosage of the product 440. Therefore, the dosage 445 includes a toggleable header 446 and a plurality of dosage fields 448. The dosage fields 448 may be substantially the same as the case detail fields 422 and are editable fields (e.g., text fields, date fields, etc.) that are automatically populated with the generated case information received from the provider computing system 104. The dosage fields 448 are automatically populated with the generated case information (i.e., case medical product dosage information) and provided to the user via the user computing device 108 for review, editing, and verification.

Figure 4A:
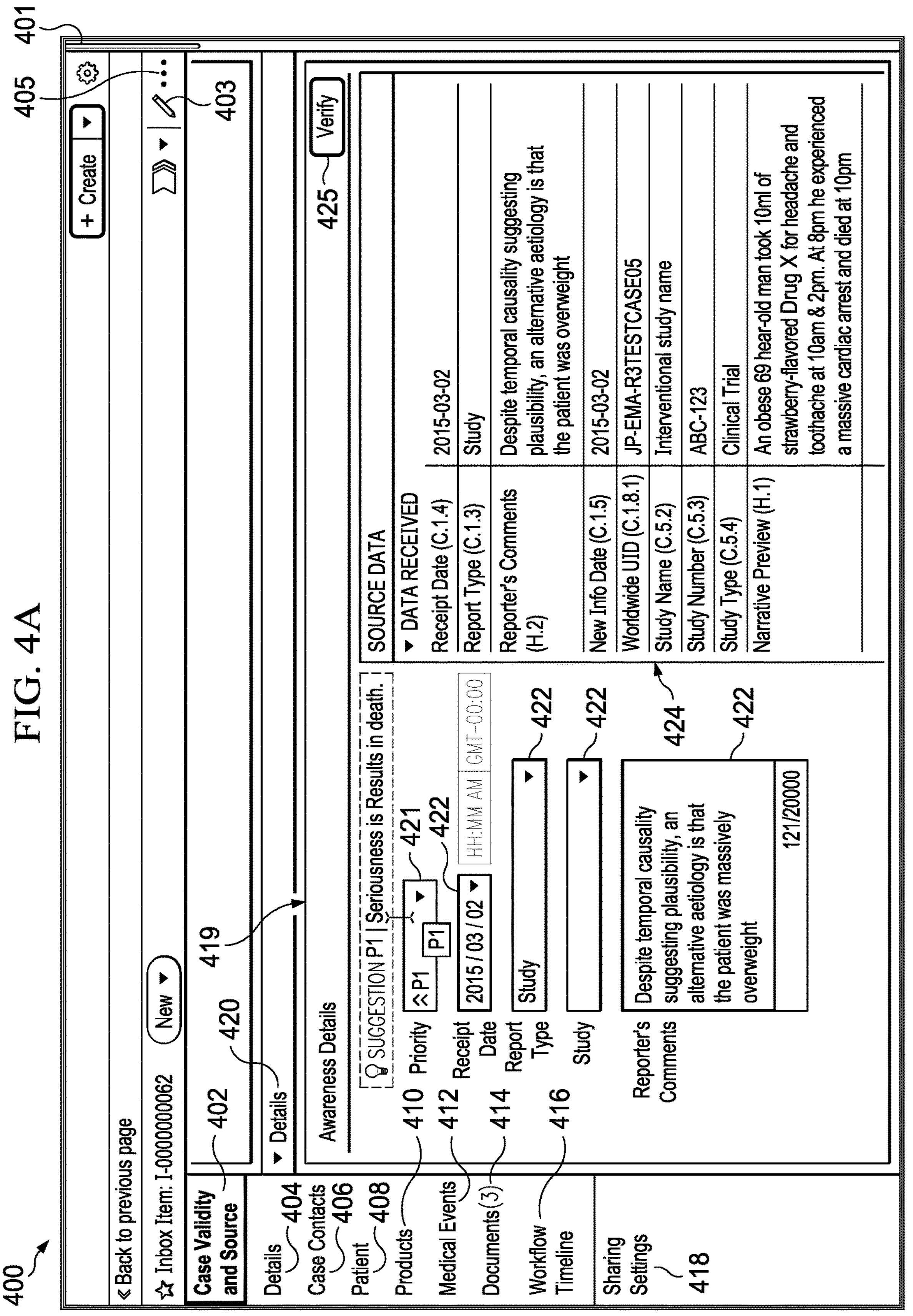
FIGS. 4A-4G are multiple illustrations of some aspects of a user interface generated by the adverse event analyzation and arrangement system of FIG. 1 after receipt of a source file, according to an example embodiment.
Figure 4B:
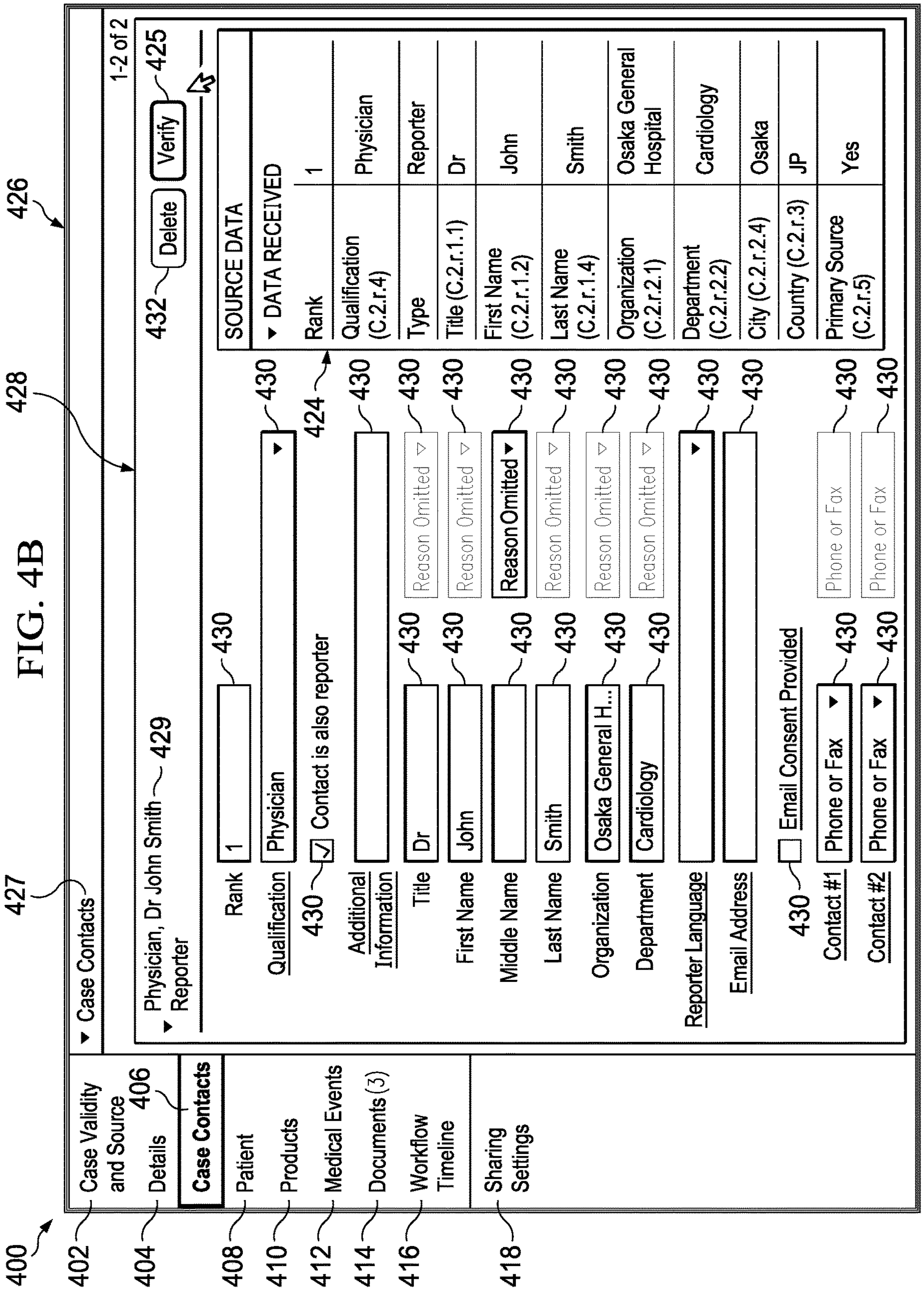
Figure 4C:
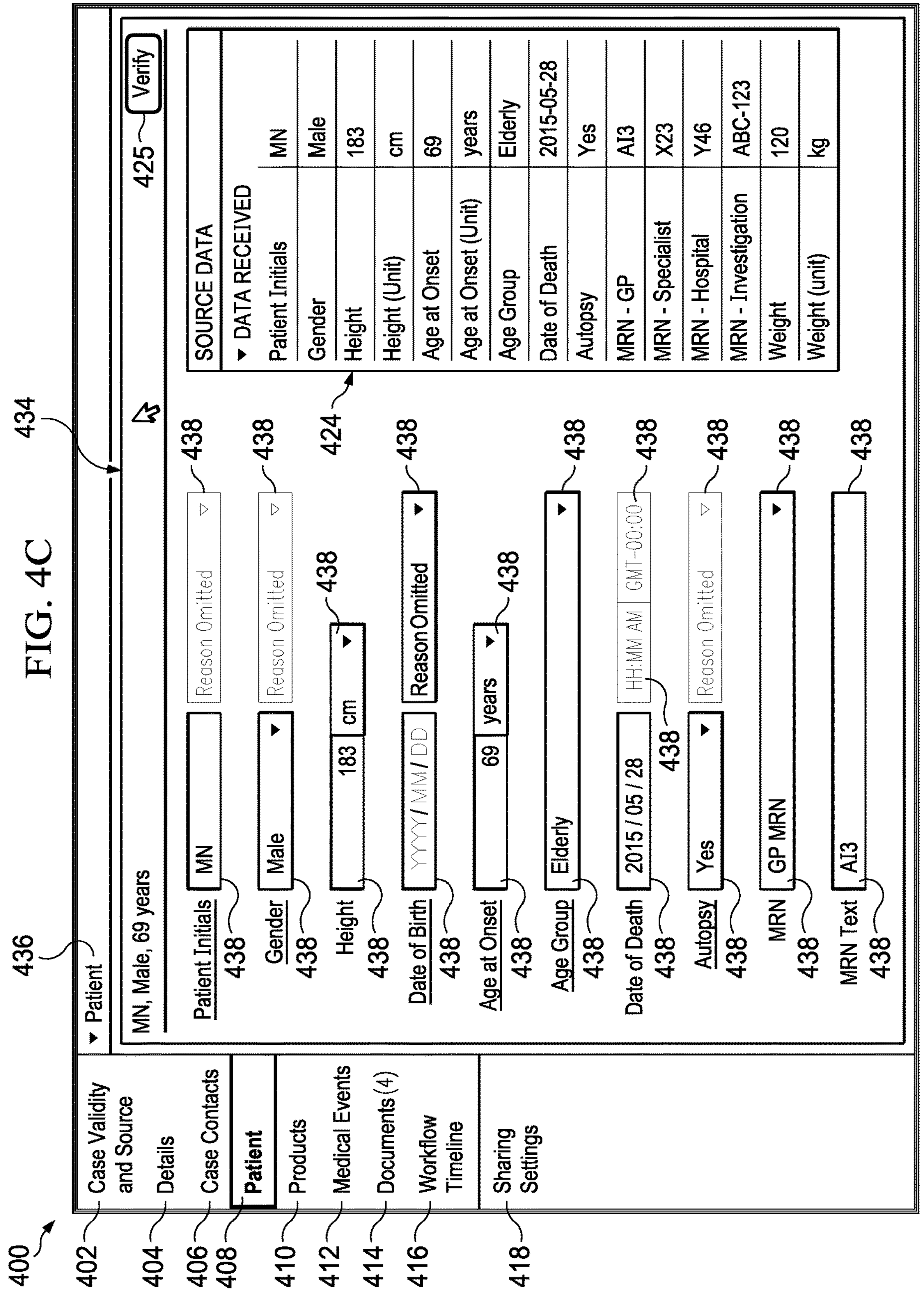
Figure 4D:
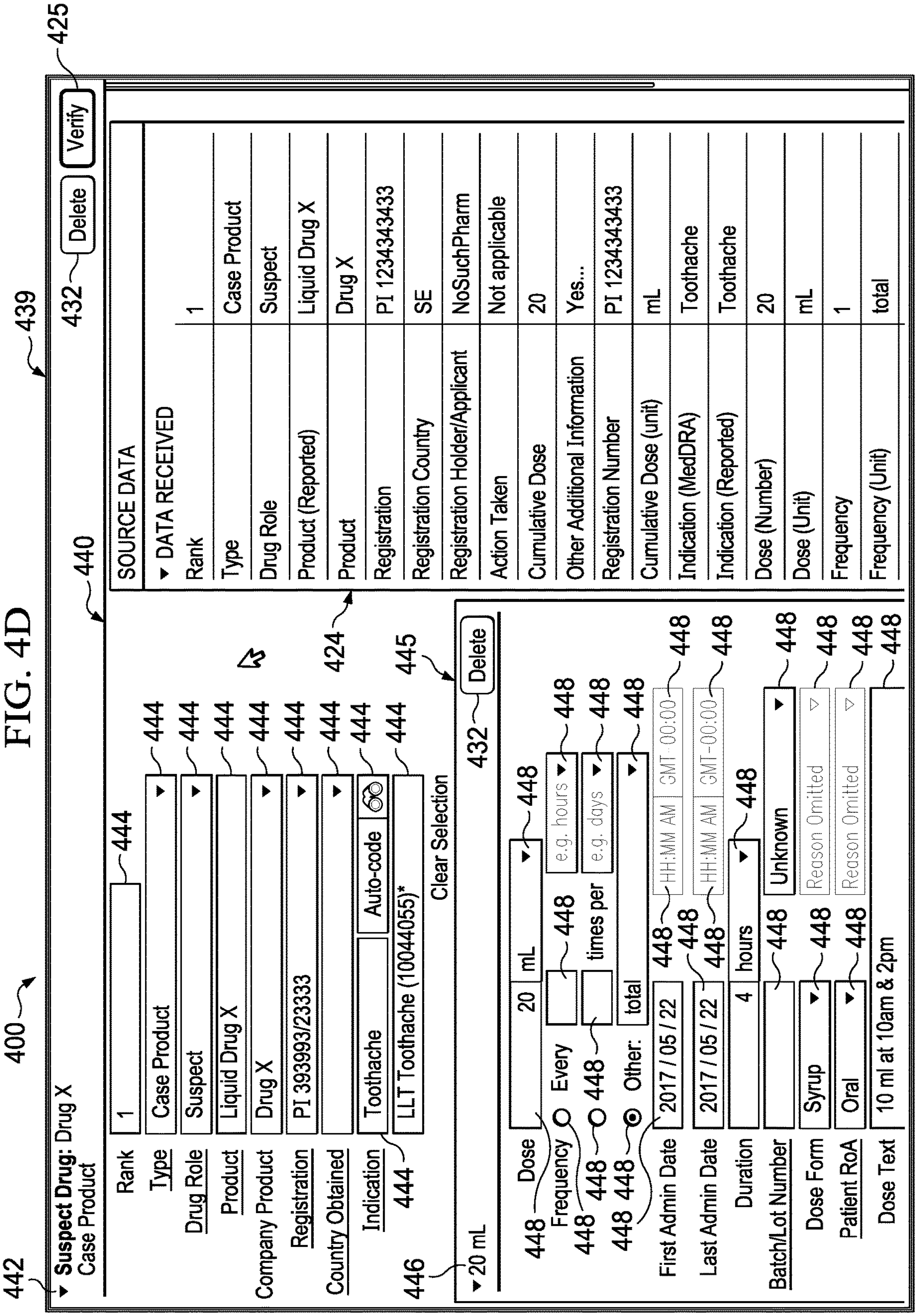
Figure 4E:
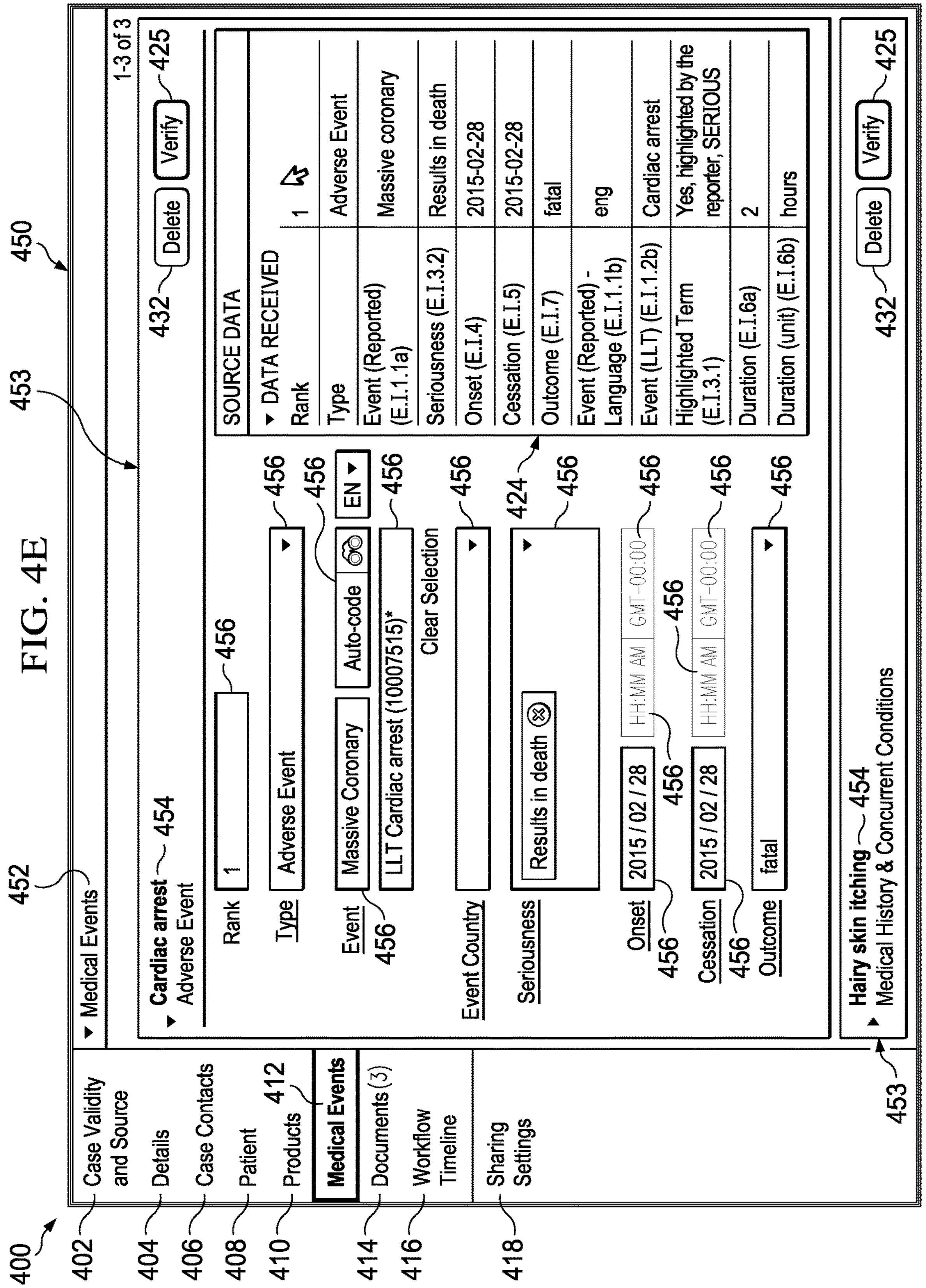
Figure 4F:
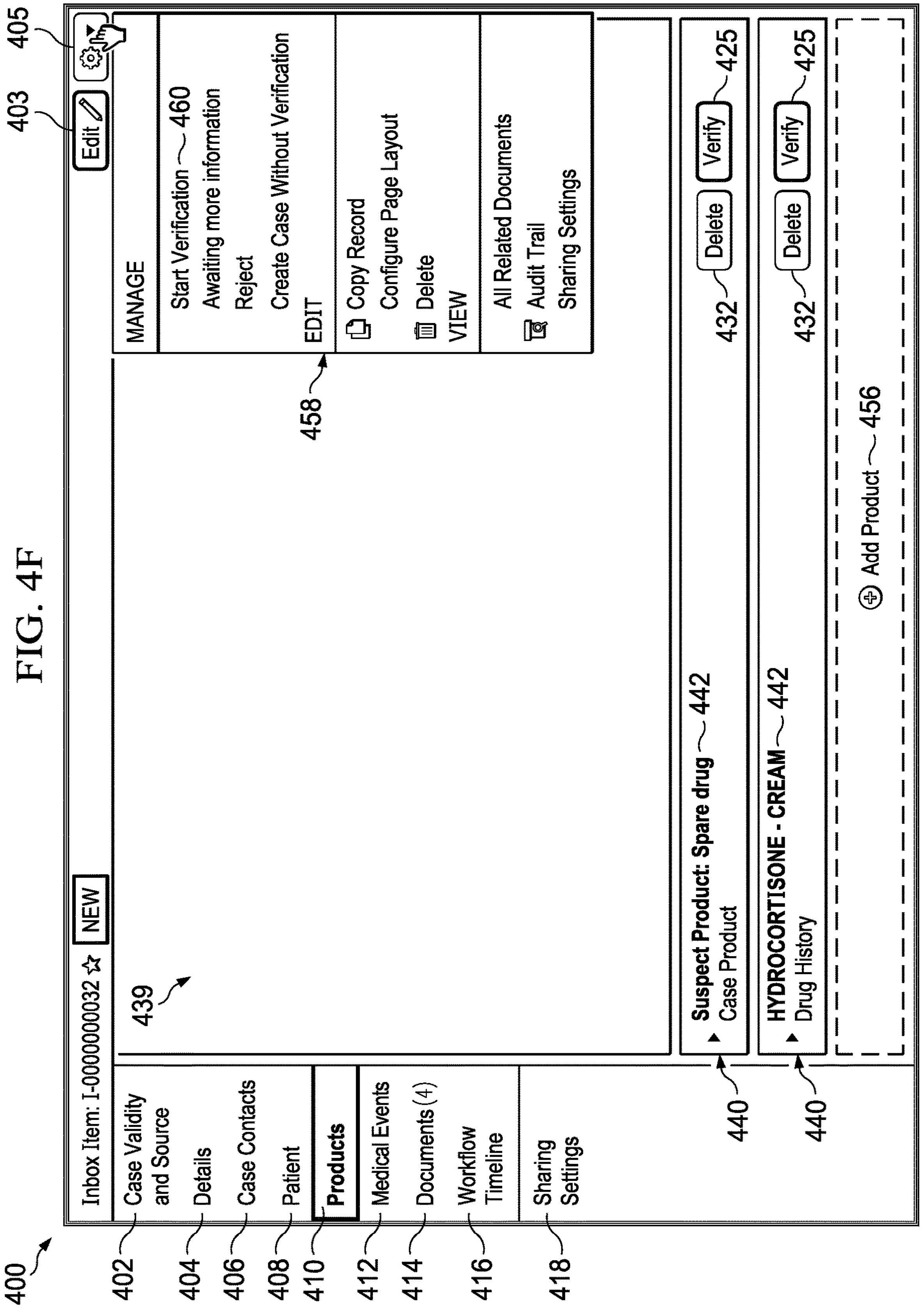
Figure 4G:
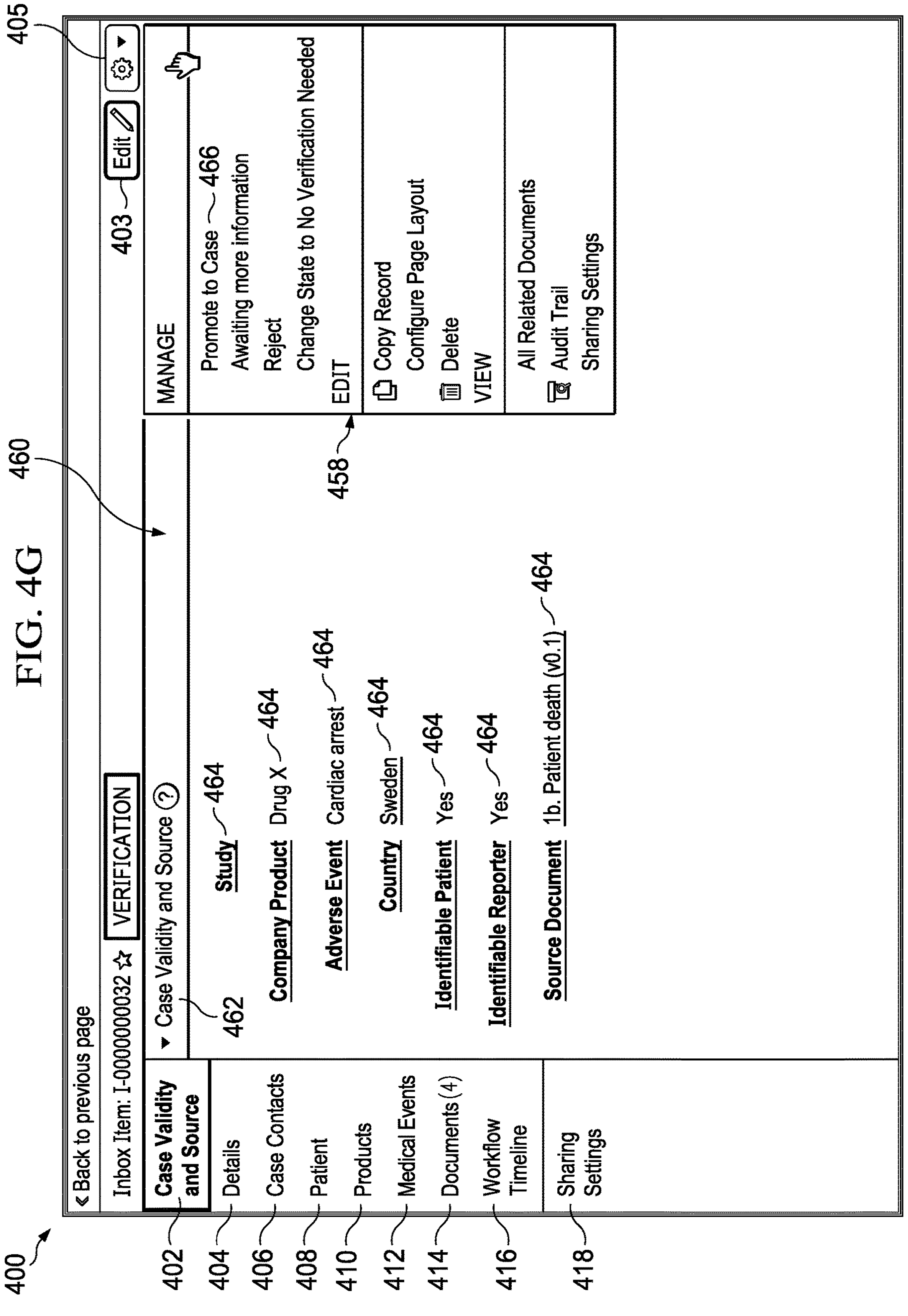

Referring to FIG. 4F, the products section 439 is further shown to include an add product button 456. The add product button 456 is a selectable that, when pressed, causes the provider computing system 104 or the user computing device 108 to generate and display a new product section. The new product section may include one or more product fields (e.g., similar to the product fields 444) that are empty. The user may then fill the fields out and generate a new product 440. While the products section 439 is the only section that is shown to include an add button, it should be understood that each of the case contacts section 426 and the medical events section 450 may include an add button through which additional case contacts and additional medical events, respectfully, may be added.

The medical events button 412 is a selectable button that navigates (e.g., automatically scrolls the user and the inbox item page 400) to a medical events section 450 of the inbox item page 400. The medical events section 450 is shown to include a toggleable header 452 and one or more medical event representations 453. Each medical event representation 453 may include a toggleable header 454, multiple medical event fields 456, and the source data viewer 424. In general, the medical events section 450 displays and provides the user with case medical event information for each medical event representation 453 for management and review. Further, if the user has fully reviewed the medical events section 450, the toggleable header 452 is a selectable and toggleable button that shows or hides the medical events section 450. Similarly, if the user has fully reviewed the medical event representation 453, the toggleable header 454 is a selectable and toggleable button that shows or hides information pertaining to the medical event representation 453.

The medical event fields 456 may be substantially the same as the case detail fields 422 and are editable fields (e.g., text fields, date fields, etc.) that are automatically populated with the generated case information received from the provider computing system 104. The medical event fields 456 are automatically populated with the generated case information (i.e., case adverse event information) and provided to the user via the user computing device 108 for review, editing, and verification. The medical event fields 456 and the related case information are shown to include a rank field. The rank field may dictate the order in which the medical event representation 453 are arranged on the inbox item page 400 and on the case itself (e.g., rank one is listed above rank two, which is listed above rank three, and so on). In some embodiments, the rank may be generated based on the type, severity, or outcome of the medical event within the adverse event information. For example, the medical event listed that had an outcome of death may be listed as rank one. In other embodiments, the rank for each medical event is assigned based on based on the date in which the medical event occurred or started to occur or based on alphabetization of medical event names.

Referring again to FIG. 4F, the edit button 403 is a selectable button 403 that may allow each field of the inbox item page 400 to be edited. Similarly, the options button 405 is a selectable button that, when selected, may provide a drop-down menu 458 with one or more selectable options associated with the inbox item to the user. In the example shown, the drop-down menu 458 includes a selectable start verification option 460. The start verification option 460, when pressed, may begin verification of the case information. In some embodiments, when the start verification option 460 is pressed, the provider computing system 104 determines if the case information includes the required adverse event information. For example and referring to FIG. 4G, the required adverse event information may include an associated study, a company product (e.g., user medical product), an adverse event, a country, identifiable patient information, an identifiable reporter information, and a source document. If the case information includes each portion of required adverse event information and the start verification option 460 is pressed, the user computing device 108 may then send an indication of verification to the provider computing system 104. If not, the inbox item page 400 may provide an indication or notification to the user that certain required adverse event information is missing.

In that regard, the case validity and source button 402 is a selectable button that navigates (e.g., automatically scrolls the user and the inbox item page 400) to a case validity section 460 of the inbox item page 400. The case validity section 460 is shown to include a toggleable header 462 and multiple case validity fields 464. In general, the case validity section 460 displays and provides the user with required adverse event information as well as the status of each for management and review. Further, if the user has fully reviewed the case validity section 460, the toggleable header 462 is a selectable and toggleable button that shows or hides the case validity section 460.

The case validity fields 464 may be substantially the same as the case detail fields 422 or may be fields that are not editable but instead are populated from other fields within the inbox item page 400. The case validity fields 464 may be automatically populated with the generated case information of the inbox items page 400 and provided to the user via the user computing device 108 for review. In some embodiments, if all the of the case validity fields 464 are not populated, the user computing device 108 may not send an indication of verification to the provider computing system 104 when the start verification option 460 is pressed.

If the case information includes each portion of required adverse event information and the start verification option 460 is pressed, the user computing device 108 may then send an indication of verification to the provider computing system 104 and the inbox item (e.g., adverse event information, the case information, and the priority of the case) may be considered verified. In some embodiments, verifying the inbox item further includes the user computing device 108 sending a timestamp of the verification and user account information to the provider computing system 104 to be recorded. Once the inbox item is verified, the drop-down menu 458 includes a promote to case option 466 in place of the start verification option 460. The promote to case option 466 is a selectable option that, when selected, signals the provider computing system 104 to begin generating a case including the case information, the adverse event information, and the case priority.

Figure 5:
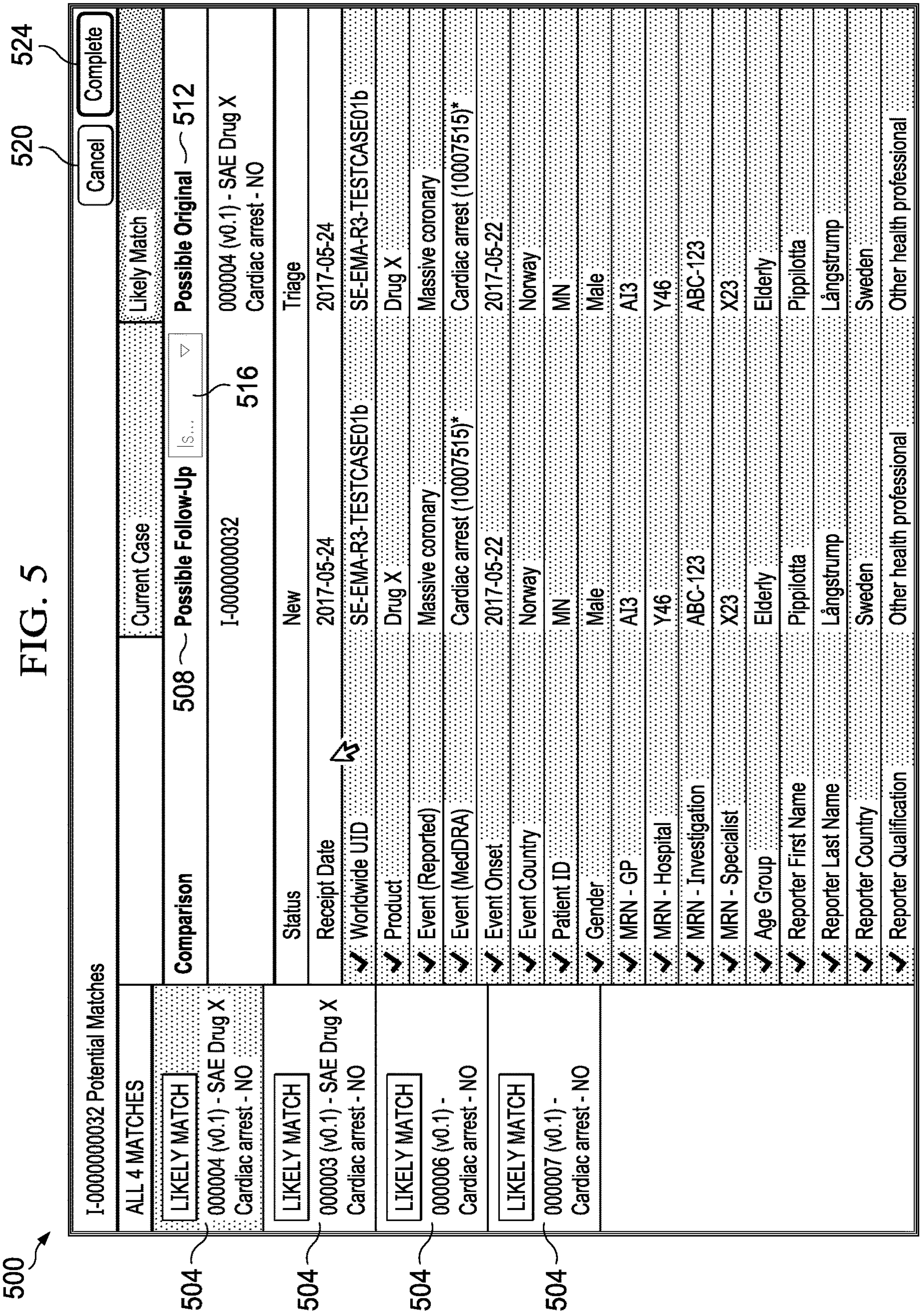
FIG. 5 is an illustration of some aspects of a user interface generated by the adverse event adverse event analyzation and arrangement system of FIG. 1 during generation of a case, according to an example embodiment.

Referring now to FIG. 5, a case duplication page 500, which can be displayed on a display of the I/O circuit 148 of the user computing device 108, is shown. In general, the case duplication already generated case. To get to the case duplication page 500, the user may navigate by pressing the promote to case option 466.

The case duplication page 500 includes multiple potential duplicate cases 504 (which are each selectable to generate a comparison), and a comparison between the current case (e.g., the case to be generated) 508 and a similar case 512. As shown, the case duplication page 500 displays case information for the current case 508 and the similar case 512 for side-by-side comparison. This allows the user to review the details of each case and determine if the current case 508 is a duplicate of the similar case 512. Once the user has made a decision, the user may select the drop down box 516 and select an option (e.g., new case, duplicate case, unsure, etc.). Once selected, the user may then select the cancel button 520 or the complete button 524. The cancel button 520 cancels the case generation process and returns the user to the inbox item page 400. The complete button 524 indicates the case is either a duplicate or a new case and, in the case of a new case, proceeds with the generation of the new case.

Figure 6:
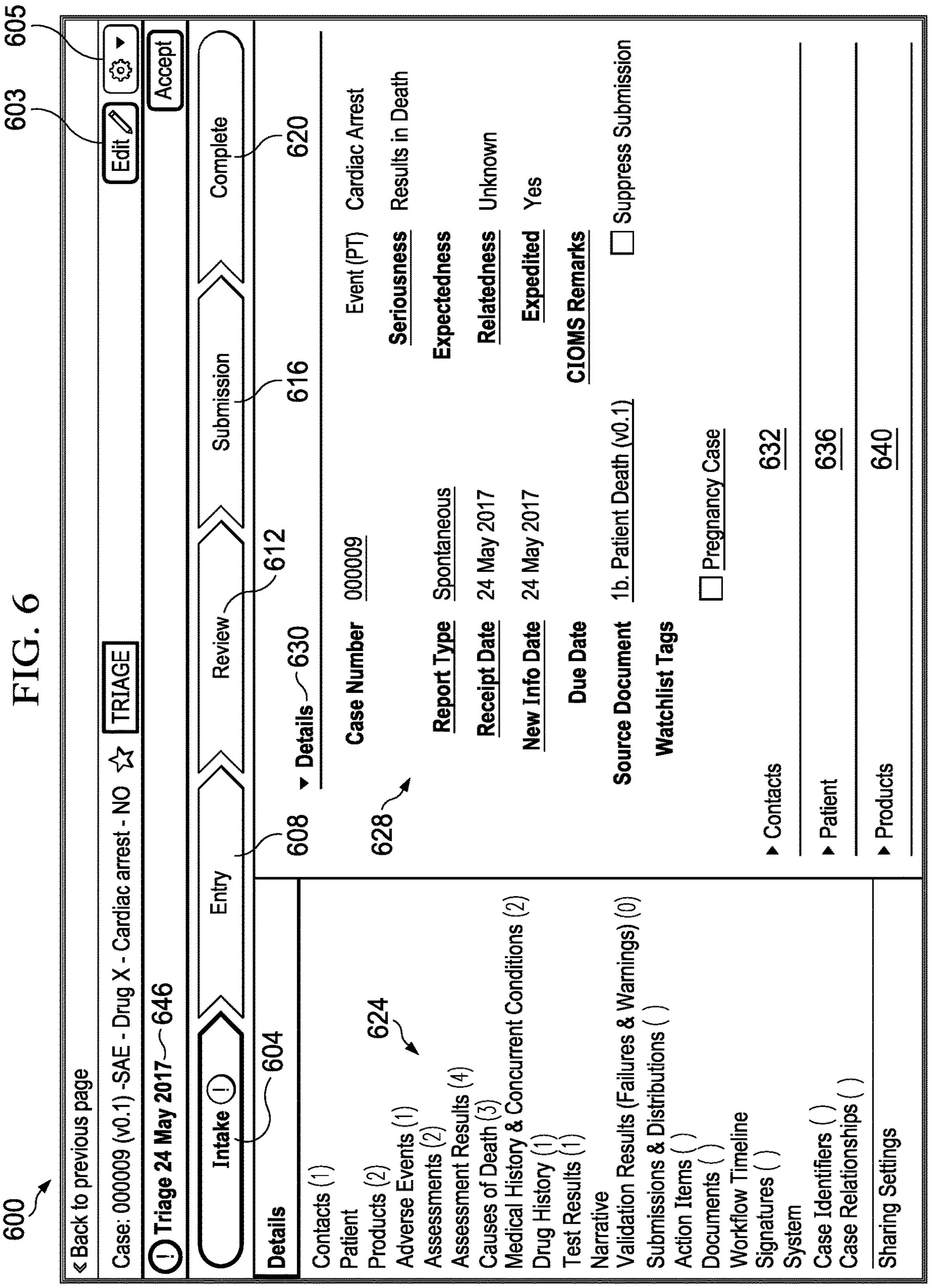
FIG. 6 is an illustration of some aspects of a user interface generated by the adverse event adverse event analyzation and arrangement system of FIG. 1 after generation of a case, according to an example embodiment.

Referring now to FIG. 6, a case page 600, which can be displayed on a display of the I/O circuit 148 of the user computing device 108, is shown. In general, the case page 600 provides the user with management (e.g., review, verification, revision, etc.) of a case. To get to the case page 600, the user may navigate via the case management page (e.g., by selecting the case on the case management page) or pressing the complete button 524 on the case duplication page 500.

The case page 600 is shown to include an edit button 603 (which may be similar to the edit button 403), an intake stage 604, an options button 605 (which may be similar to the options button 405), an entry stage 608, a review stage 612, a submission stage 616, and a complete stage 620. The stages will not be described herein, but it should be understood that the various stages of the case page 600 are stages that the case may go through during the cases lifecycle. For example, the submission stage 616 may be the stage at which the case is provided, by the provider computing system 104, to the third-party computing system 112 (e.g., the FDA) via an AS2 gateway communication.

The case page 600 is further shown to include a case information menu 624, a case details section 628, a case contacts section 632, a case patient section 636, and a case product section 640. The case information menu 624 may include multiple buttons that navigate the user to the various sections of the case page 600 (e.g., the details button navigates the user to the case details section 628).

The case details section 628, the case contacts section, the case patient section 636, and the case product section 640 may be the similar (and include the same information as) their respective inbox item sections (of the inbox item page 500) and may include information pertaining to the case. In this way, each section may provide for management (e.g., review, verification, editing) of the case information of the case.

The case page 600 is further shown to include a banner 646 with an assigned date/time (e.g., 24 May 2017) or timeframe. As described herein, the timeframe of the banner 646 may be defined by the priority of the case and may indicate a required timeframe for the case to be reviewed.

Figure 7:
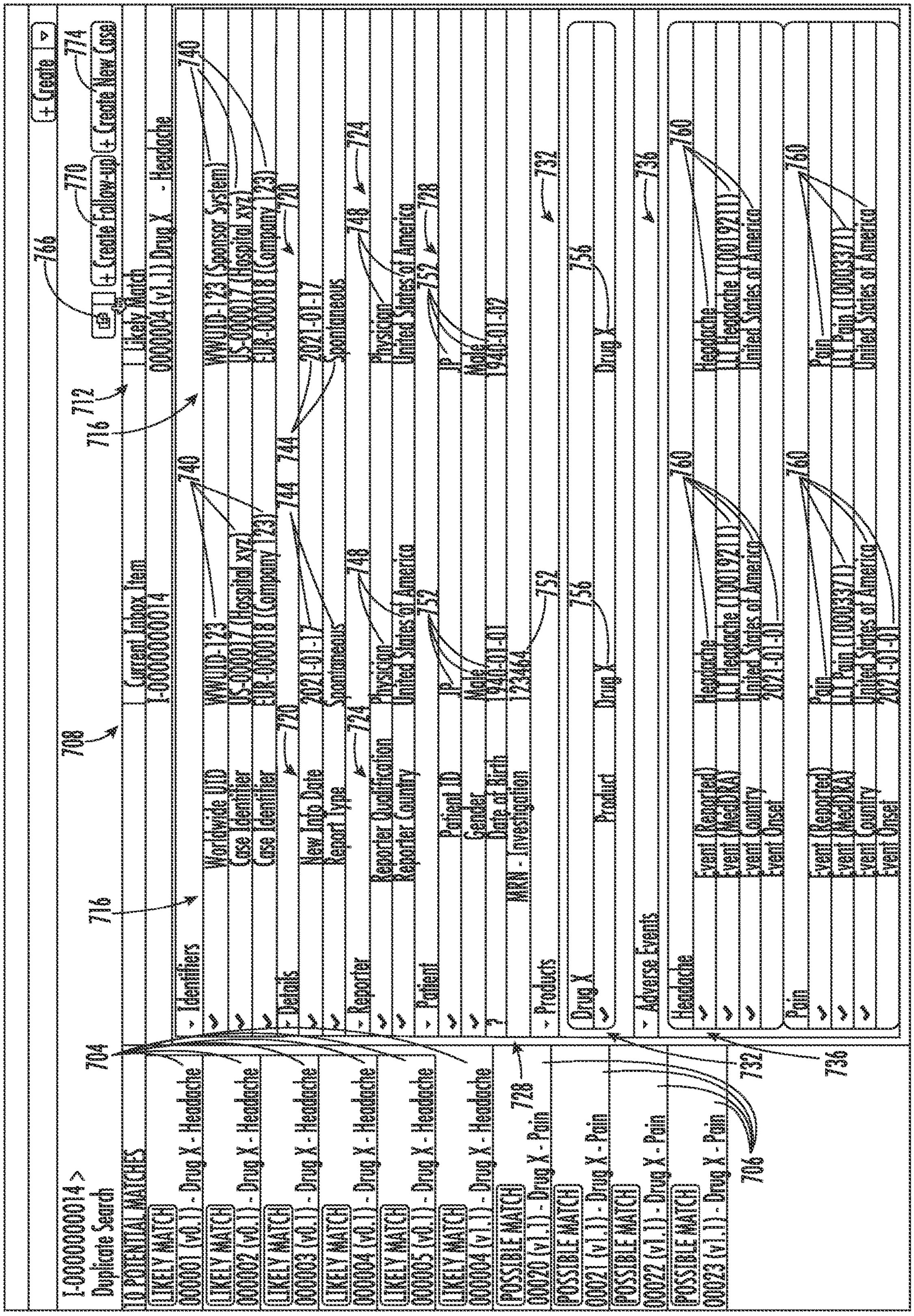
FIG. 7 is an illustration of some aspects of a user interface generated by the adverse event adverse event analyzation and arrangement system of FIG. 1 during generation of a case, according to an example embodiment.

Referring now to FIG. 7, a second case duplication page 700, which can be displayed on a display of the I/O circuit 148 of the user computing devices 108, is shown. In general, the case duplication page 700 provides one or more of the user computing devices 108 with an interface to view, select, and manage one or more potential duplicate cases of the specific case and provide a type of the specific case (e.g., follow-up, new case, duplicate case, etc.) to the provider computing system 104. As a result, the second case duplication page 700 may be similar to the case duplication page 500, and description and details of one may be applied to the other (i.e., description and functionality of the case duplication page 500 may be applied to the case duplication page 700, and vice versa). As shown, the case duplication page 700 includes multiple likely duplicate cases/case representations 704 (which are each selectable to generate a comparison), multiple possible duplicate cases/case representations 706 (which are each selectable to generate a comparison), a comparison between the current or specific case (e.g., the case to be generated) 708 section and a potential matching case 712 section, a mark as duplicate button 766, a create-follow-up case button 770, and a create new case button 774.

The difference between likely (also referred to as first categorized or classified) duplicate cases and possible (also referred to as second categorized or classified) duplicate cases will be described further herein with regard to method 800, but it should be understood that likely duplicate cases as represented by the multiple likely duplicate case representations 704 have a higher ranking (e.g., have more matching case information and/or adverse event data) than the possible duplicate cases as represented by the multiple possible duplicate case representations 706, while each is a potential matching case. In this regard, each likely duplicate case representation 704 is a selectable button that represents a likely duplicate case and, when selected, is displayed by the user computing device 108 on the user interface (e.g., within the potential matching case comparison section 712). Further, each possible duplicate case representation 706 is a selectable button that represents a possible duplicate case and, when selected, is displayed by the user computing device 108 on the user interface (e.g., within the potential matching case comparison section 712). In this regard, each likely duplicate case representation 704 and possible duplicate case representation 706 each include a quick summary of the respective potential matching case (e.g., case number, primary or highest ranking medical product associated with the case (e.g., "drug x"), and/or primary or highest ranking adverse event associated with the case (e.g., "headache")).

In some embodiments, when either of the likely duplicate case representation 704 or the possible duplicate case representation 706 is pressed, the user computing device 108 may provide an indication of such to the provider computing system 104, which may provide the case information and/or adverse event information associated with the specific potential duplicate case to the user computing device 108 for display in the potential matching case comparison section 712. In other embodiments, the provider computing system 104 may automatically send the case information and/or adverse event information associated with each of the multiple likely duplicate case representations 704 and the multiple possible duplicate case representations 706 to the user computing device 108 after determining each is a match and ranking each (as will be described further herein with respect to the method 800).

The current or specific case comparison section 708 provides the user of the user computing device 108 with line-by-line case information and/or adverse event information associated with the specific or current case to compare with the selected potential matching case in the potential matching case comparison section 712. In this regard and as shown, each of the current or specific case comparison section 708 and the potential matching case comparison section 712 include an identifiers comparison section 716, a case details comparison section 720, a reporter comparison section 724, a patient comparison section 728, a medical product(s) comparison section 732, and an adverse event(s) comparison section 736.

Each of the identifiers comparison sections 716 includes multiple identifier fields 740, which each include and display identifier information associated with the respective case (e.g., the current case or the potential matching case), in a line-by-line fashion. For example and as shown, the current case represented by the current case comparison section 708 includes a worldwide UID identifier field 740, a first case identifier field 740 associated with hospital xyz, and a second case identifier field 740 associated with company 123. Likewise, the selected potential matching case represented by the potential matching case comparison section 712 also includes a worldwide UID identifier field 740, a first case identifier field 740 associated with hospital xyz, and a second case identifier field 740 associated with company 123. In some embodiments, each of the identifier fields 740 is read-only and cannot be edited by the user of the user computing device 108.

Similarly, each of the case details comparison sections 720 includes multiple case information fields 744, which include and display case information (e.g., case details such as those of the details section 419) associated with the respective case (e.g., the current case or the potential matching case), in a line-by-line fashion. For example and as shown, the current case represented by the current case comparison section 708 includes a new info date case information field 744 and a report type case information field 744. Likewise, the selected potential matching case represented by the potential matching case comparison section 712 also includes a new info date case information field 744 and a report type case information field 744. In some embodiments, each of the case information fields 744 is read-only and cannot be edited by the user of the user computing device 108.

Likewise, each of the reporter comparison sections 724 includes multiple reporter information fields 748, which each include and display reporter information associated with the respective case (e.g., the current case or the potential matching case), in a line-by-line fashion. For example and as shown, the current case represented by the current case comparison section 708 includes a reporter qualification field 748 and a reporter country field 748. Likewise, the selected potential matching case represented by the potential matching case comparison section 712 also includes a reporter qualification field 748 and a reporter country field 748. In some embodiments, each of the reporter information fields 748 is read-only and cannot be edited by the user of the user computing device 108. Further, each reporter comparison section 736 may compare reporters regardless of the rank of the reporter. For example, if the current case includes a reporter with a priority "2" and the potential matching case includes the same reporter with a priority "1", each reporter comparison section 736 may include the respective reporter and show each the cases as including matching reporters.

Still referring to FIG. 7, each of the patient comparison sections 728 includes multiple patient information fields 752, which each include and display patient information associated with the respective case (e.g., the current case or the potential matching case), in a line-by-line fashion. For example and as shown, the current case represented by the current case comparison section 708 includes patient ID patient information field 752, a gender patient information field 752, a date of birth patient information field 752, and an MRN-investigation patient information field 752. Likewise, the selected potential matching case represented by the potential matching case comparison section 712 also includes patient ID patient information field 752, a gender patient information field 752, and a date of birth patient information field 752, while not including an MRN-investigation patient information field 752. In some embodiments, each of the patient information fields 752 is read-only and cannot be edited by the user of the user computing device 108.

Similarly, each medical product(s) comparison section 732 includes one or more medical product information fields 756, which include and display medical product information associated with the respective case (e.g., the current case or the potential matching case), in a line-by-line fashion. For example and as shown, the current case represented by the current case comparison section 708 includes a product medical product information field 756. Likewise, the selected potential matching case represented by the potential matching case comparison section 712 also includes a product medical product information field 756. In some embodiments, each of the medical product information fields 756 is read-only and cannot be edited by the user of the user computing device 108. In some embodiments, each medical product(s) comparison section 732 includes a line-by-line comparison (and a medical product information field 756) of each medical product associated with the case (e.g., the primary or highest ranked medical product associated with the case, a second medical product associated with the case, and so on. Further, each medical product(s) comparison section 732 may compare medical products regardless of the rank of the medical product. For example, if the current case includes a medical product with a rank "2" and the potential matching case includes the same medical product with a rank "1", each medical product(s) comparison section 732 may include the respective medical product and show each the cases as including matching medical products.

Likewise, each adverse event(s) comparison section 736 includes multiple adverse event information fields 760, which include and display adverse event information associated with the respective case (e.g., the current case or the potential matching case), in a line-by-line fashion. For example and as shown, the current case represented by the current case comparison section 708 includes two event (reported) adverse event information fields 760, two event code adverse event information fields 760, two event country adverse event information fields 760, and two event onset adverse event information fields 760. Likewise, the selected potential matching case represented by the potential matching case comparison section 712 also includes two event (reported) adverse event information fields 760, two event code adverse event information fields 760, two event country adverse event information fields 760, while not including an event onset adverse event information field 760. In some embodiments, each of the adverse event information fields 760 is read-only and cannot be edited by the user of the user computing device 108. In some embodiments, each adverse event(s) comparison section 736 includes a line-by-line comparison (and an adverse event information field 760) of each adverse event associated with the case (e.g., the primary or highest ranked/priority adverse event associated with the case, a second adverse event associated with the case, and so on. For instance, each adverse event(s) comparison section 736 includes a line-by-line comparison of the adverse event "headache" and "pain," as shown in FIG. 7. Further, each adverse event(s) comparison section 736 may compare adverse events regardless of the rank/priority of the adverse event. For example, if the current case includes an adverse event with a priority "2" and the potential matching case includes the same adverse event with a priority "1", each adverse event(s) comparison section 736 may include the respective adverse event and show each of the cases as including matching adverse events.

As shown, the provider computing system 104 may compare each of the fields (e.g., the identifier fields 740, the case information fields 744, the reporter information fields 748, the patient information fields 752, the medical product information fields 756, and/or the adverse event information fields 760) of the potential matching case comparison section 712 with the respective (i.e., matching or same data field) fields of the current case comparison section 708 by indicating whether the fields match, don't match, or are not included in the other respective field. For example, the provider computing system 104, may indicate the fields match line-by-line on the case duplication page 700 in a variety of ways including by including a check-mark within the line if the fields match, by coloring the line (e.g., green) (and the space within the line), by bolding the text of the line including the fields, and/or the like. In some embodiments, if the fields do not match or only partially match (e.g., the date and birth year and month are the same but the day is different, the medical product is in a different form (e.g., liquid vs capsule), and the like), the provider computing system 104 may indicate as such line-by-line on the case duplication page 700 in a variety of ways including by including a question mark or "X" within the line, by coloring the line (e.g., red, yellow, or orange) (and the space within the line), by bolding the text of the line including the fields, and/or the like. In some embodiments, if at least one of the potential matching case comparison section 712 or the current case comparison section 708 includes an identifier field which the other does not, the provider computing system 104 may indicate as such line-by-line on the case duplication page 700 in variety of ways including by including a question mark or "X" within the line, by coloring the line (e.g., red, white, yellow, or orange) (and the space within the line), by bolding the text of the line including the fields, and/or the like.

In one example, the adverse event(s) comparison section 736 of the current case comparison section 708 may include a first adverse event information field 760, and the adverse event(s) comparison section 736 of the potential matching case comparison section 712 may include a second adverse event information field 760. Further, the first adverse event information field 760 and the second adverse event information field 760 may be for the same data field, may be directly adjacent and/or on the same line, and may match (e.g., may include the same adverse event MedDRA code, may include the same event country, etc.). As a result, the line on which the first adverse event information field 760 and the second adverse event information field 760 are included may include a check mark, may be colored green, and/or may include emphasized text fields (i.e., the first adverse event information field 760 and the second adverse event information field 760).

By comparing the potential duplicate case and the case to be generated in a field-by-field and line-by-line manner, the provider computing system 104 provides an easy-to-comprehend comparison and analysis of the differences and similarities between the case to be generated and the selected potential duplicate case, which allows the user of the user computing device 108 to quickly analyze the two cases and make a decision on whether the potential duplicate is a duplicate, is a related case, or is not a duplicate. For example and as shown, via the comparison of the two cases on the case duplication page 700, the user can quickly infer the only difference between the two cases is the case to be generated has a different patient date of birth, includes an MRN investigation number for the patient, and includes event onset information for each of the adverse events.

Still referring to FIG. 7, the mark as duplicate button 766, the create-follow-up case button 770, and the create new case button 774 are each selectable buttons that, when selected, indicate or provide the type of the current or specific case to the provider computing system 104 from the user computing device 108. For example, via the case duplication page 700, the user may determine the current case is a duplicate of one of the potential duplicate cases and select the mark as duplicate button 766. In response, the user computing device 108 may provide the type (e.g., duplicate case) of the current case to the provider computing system 104 which may indicate the generated case information or adverse event information is associated with a duplicate case and that no case is to be generated. In another example, via the case duplication page 700, the user may determine the current case is a follow-up case of one of the potential duplicate cases and select the create follow-up button 770. In response, the user computing device 108 may provide the type (e.g., follow-up case) of the current case to the provider computing system 104 which may indicate the generated case information or adverse event information is associated with a follow-up case and that a new case is to be generated which is linked to the potential duplicate case. In another example, via the case duplication page 700, the user may determine the current case is a new case (i.e., not a duplicate or follow-up of one of the potential duplicate cases) and select the create new case button 774. In response, the user computing device 108 may provide the type (e.g., new case) of the current case to the provider computing system 104 which may indicate the generated case information or adverse event information is associated with a new case and that a new case is to be generated which is not linked to any other cases.

Figure 8:
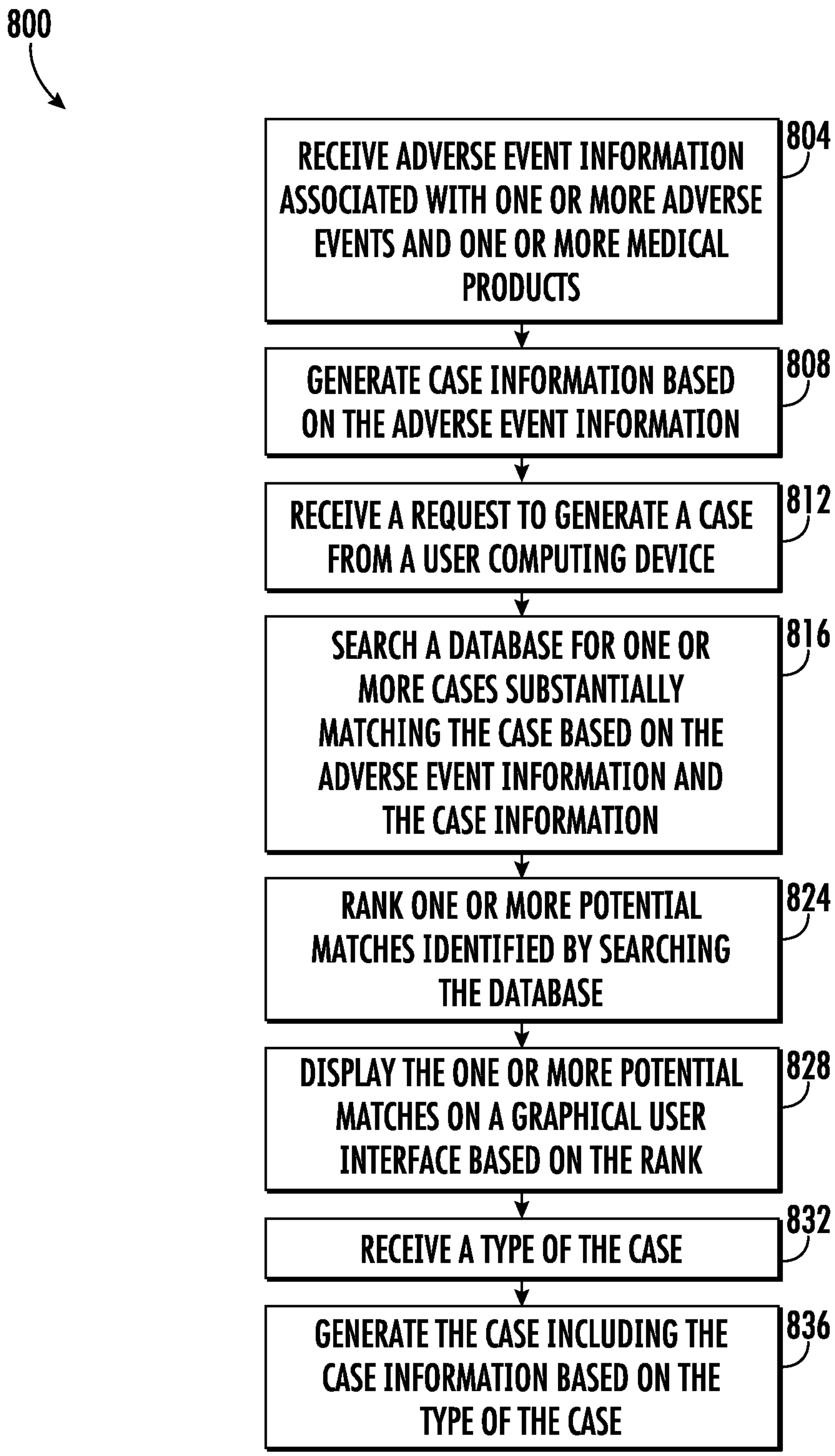
FIG. 8 is a flow diagram of a method for analyzing adverse event information, detecting potential duplicate cases, and generating a related case, according to an example embodiment.

Referring now to FIG. 8, a method 800 of analyzing an adverse event and generating a related case is shown, according to an example embodiment. While different overall, it should be understood that any steps or discussion of the method 800 may be applied or included within the method 200, and vice versa, and that such combinations are included within the scope of the present disclosure. For example, the method 200 may include any of the steps 804-836, after or before any steps included in the method 200, and the method 800 may include any of the steps 204-240, after or before any of the steps included in the method 800. Method 800 can be carried out by the system of FIG. 1. More particularly, the method 800 can be carried out by the processing circuit 122 of the provider computing system 104 and through communication with the user computing device 108 and the third-party computing system 112.

Method 800 commences at step 804 at which the provider computing system 104 receives adverse event information associated with one or more adverse events and one or more medical products. In some embodiments, the adverse event information may be received in a source file and determined by the provider computing system 104 (e.g., the same as steps 204 and 208 of the method 200). In some embodiments, the adverse event information is associated with one or more clinical studies or trials, and each clinical study or trial is associated with one or more medical products. In some embodiments, the adverse event information is associated with multiple medical products (e.g., a first medical product and a second medical product) and multiple adverse events (e.g., a first adverse event, and a second adverse event.)

Once the provider computing system 104 has received the adverse event information, the method 800 proceeds to step 808 at which the provider computing system 104 generates case information based on the adverse event information. In some embodiments, the provider computing system 104 may determine if the adverse event information is complete prior to proceeding to step 808 (e.g., as is done in steps 212-220 of the method 200). In some embodiments, the provider computing system 104 generates the case information based on the adverse event information (and the missing or corrected adverse event information received from the user computing device 108). As described herein, the case information may include the adverse event information as well as other information pertaining to the ICSR such as the case contact and the case documents (e.g., the source file). In some embodiments, the provider computing system 104 may generate case information by transforming adverse event information that is in an incorrect format into a correct format (e.g., “SE” to “Sweden”). In this regard, step 808 may be the same as step 224 of the method 200. In some embodiments, at step 808, the provider computing system 104 may further generate a priority of the case based on the adverse event information (e.g., as discussed with regard to step 228 of the method 200), a rank of the adverse events associated with the current case, a rank of the medical products, and the like.

Once the provider computing system 104 has generated the case information, the method 800 proceeds to step 812 at which the provider computing system 104 receives a request to generate a case from the user computing device 108. In some embodiments, in response to receiving the request, the provider computing system 104 may verify the case information or the adverse even information. In some embodiments, the request may be generated and provided to the provider computing system 104 in response to the user of the user computing device 108 selecting the promote to case option or button 466 of the inbox item page 400.

Once the provider computing system 104 has received the request to generate the case, the method 800 proceeds to step 816 at which the provider computing system 104 searches or queries a database (e.g., the account database 137 or a case database (not shown)) for one or more cases substantially matching (e.g., potential matches of) the case to be generated based on the adverse event information and/or the case information, and selects or determines the one or more of the potential matches. In this regard, substantially matching or potential matching cases may be cases in which one or more pieces of the case information and/or adverse event information match, but other pieces do not. For example, a substantially matching or potentially matching case may include the same adverse events based on the adverse event information of each, but a different report type.

To search or query for the one or more potential matches, the provider computing system 104 may first determine if the current case has a unique identifier (UID) (e.g., a worldwide UID, a specific computing system UID (e.g., a UID associated with the third-party computing system 112, etc.) and the like), and if so, search the database for any cases that match the UID (e.g., also include the same UID). Further, the provider computing system 104 may search within or query the database in other ways. For example, the provider computing system 104 may search or query the database for cases that include the same case information (e.g., same report type, same receipt or new info date, and/or the like), cases that include the same patient information (e.g., same patient ID, same gender, same medical record number (MRN), and/or the like) cases that include the same reporter information (e.g., same reporter qualification, same reporter name, same reporter country, and/or the like) regardless of the rank of the reporter, cases that include the same medical product information (e.g., same medical product name, same medical product dosage, same chemical formula, and/or the like) regardless of the rank of the medical product, and/or cases that include the same adverse event information (e.g., same reported event (e.g., “headache”), same MedDRA code, same event country, same event onset date, and/or the like). In some embodiments, the rank of the reporter is taken into consideration when searching or querying the database for cases that include the same case information (e.g., the primary reporter is the only reporter considered).

If at step 816 the provider computing system 104 searches the database and does not determine or select any matches, the method 800 may proceed to step 836, which will be discussed in further detail herein. For example, the provider computing system 104 may determine that no potentially matching cases are included in the database and that the type of the current case is a new case, as result. Further, the provider computing system 104 may automatically generate the case based on the case the type of the case being a new case.

Once the provider computing system 104 has searched the database for and selected or determined the one or more potential matches, the method 800 proceeds to step 824 at which the provider computing system 104 ranks the one or more potential matches based on the adverse event information and/or the case information of the current case and the one or more potential matching cases. In some embodiments, at or prior to step 824, the provider computing system 104 first categorizes or classifies the one or more potential matching cases into a first category or classification and a second category or classification, prior to ranking each of the potential matching cases. In some embodiments, the provider computing system 104 may categorize and rank the potential matches, even if there is a single potential match. In some embodiments, the provider computing system 104 may cut the number of potential matching cases after categorizing and ranking the cases by removing the lowest ranked potential matching cases. For example, the provider computing system 104 may only provide or display the 20 highest ranking potential matching cases at the step 828, and therefore remove the lowest ranking cases until 20 potential matching cases remain. In other embodiments, the provider computing system 104 may only provide/keep or display a specific number of potential matching cases (e.g., 5, 10, 15, 20, 25, 30, etc.).

To categorize the potential matches, the provider computing system 104 may compare the case information and the adverse event information of the current case and the one or more potential matches and score the potential matches based on the results. For example, the provider computing system 104 may first determine if the potential matching cases are possible matches (e.g., a second category) or likely (e.g., a first category) matches, as described with reference to the case duplication page 700. To determine if a potential matching case is a likely match, the provider computing system 104 may compare the UID(s) of the current case and the one or more potential matches. If the potential matching case being categorized includes a matching UID with that of the current case, the potential matching case may be considered a likely match. Further, the provider computing system 104 may compare the product information (or study information), the patient information, the reporter information, and/or the adverse event information of the current case and the one or more potential matches. If the potential matching case being categorized includes at least four pieces of matching information or fields, the potential matching case may be considered a likely match. For example, if the potential matching case being categorized includes a piece of matching product information or field (e.g., matching product name) or a piece of matching study information or field (e.g., matching study name), a piece of matching patient information or field (e.g., a patient name, a patient MRN, etc.), and two pieces of matching adverse event information or fields (e.g., matching MedDRA codes, the potential matching case may be considered a likely match. In some embodiments, to be categorized as a likely match, the potential matching case being categorized includes at least four matching pieces of matching information or fields of four different categories (e.g., a piece of adverse event information, a piece of reporter information, a piece of medical product information, and a piece of patient information).

Likewise, to determine if a potential matching case is a possible match the provider computing system 104 may compare and match the product information (or study information), the patient information, the reporter information, and/or the adverse event information of the current case and the one or more potential matches. If the potential matching case being categorized includes at least three pieces of matching information or fields, the potential matching case may be considered a possible match. For example, if the potential matching case being ranked includes a piece of matching product information (e.g., matching product name) or a piece of matching study information (e.g., matching study name), a piece of matching patient information (e.g., patient name), and a piece of matching adverse event information (e.g., matching MedDRA codes), the potential matching case may be considered a possible match. In another example, if the potential matching case being categorized includes a matching piece of product information (e.g., matching product name) or a matching piece of study information (e.g., matching study name) and two matching pieces of adverse event information (e.g., MedDRA code and event country), the potential matching case may be considered a possible match. In some embodiments, to be categorized as a possible match, the potential matching case being categorized includes at least three matching pieces of matching information or fields of three different categories (e.g., a piece of adverse event information, a piece of reporter information, and a piece of patient information).

Further, the provider computing system 104 may rank the likely potential matching cases and the possible potential matching cases among one another. For example, the provider computing system 104 may rank a first likely potential matching case with a matching UID, a matching product (e.g., matching product name) or study (e.g., matching study name), and a matching patient MRN or two other matching patient fields (e.g., patient id and patient gender) higher than a second likely potential matching case with a matching product (e.g., matching product name) or study (e.g., matching study name), a matching patient MRN or two other matching patient fields (e.g., patient id and patient gender), and two matching adverse event fields (e.g., MedDRA code and event country). In another example, the provider computing system 104 may rank a third possible potential matching case with a matching product (e.g., matching product name), a matching patient MRN, two other matching patient fields (e.g., patient id and patient gender), and three matching reporter fields (e.g., reporter qualification, reporter name, and reporter country higher than a fourth possible potential matching case with a matching product (e.g., matching product name), two matching adverse event fields (e.g., MedDRA code and event country), and two other matching patient fields (e.g., patient id and patient gender). In this regard, the categorized potential matching cases may be ranked based on the number of matching pieces of information and/or number of matching categories.

It should be understood that the provider computing system 104 may match, categorize, and rank the potential duplicate cases with the current case based on the product information (or study information), the patient information, the reporter information, and/or the adverse event information, regardless of the rank associated with each (e.g., as described with regard to the method 200 and the inbox item page 400). For example, the provider computing system 104 may determine a match of adverse event information associated with an adverse event ranked "2" of the current case with adverse event information associated with an adverse event ranked "1" of the potential matching case. In another example, the provider computing system 104 may determine a match of medical product associated with a medical product ranked "1" of the current case with medical product information associated with a medical product ranked "3" of the potential matching case.

By comparing the potential case and the case to be generated based on matching adverse events, reporters, and/or medical products, regardless of rank of the respective field, the method 800 provides for a more accurate and effective searching methodology and a technical improvement to case duplication searching systems overall. For example, because the provider computing system 104 determines cases are potential duplicate cases based on the adverse events, the reporters, and/or the medical products of the potential duplicate cases and the case to be generated without taking into consideration the respective ranking of each, the provider computing system 104 more effectively finds and determines duplicate cases than typical systems. For instance, a duplicate case may have an adverse event (e.g., "rash") with a rank "2," and the case to be generated may have an adverse event (e.g., "rash") with a rank "1" (e.g., the rash is the primary adverse event of the case). As a result, because the provider computing system 104 determines potential duplicate cases based on matches between the adverse events, reporters, and/or medical products, regardless of the rank assigned to each, the duplicate case described above would be detected by the provider computing system 104.

Once the provider computing system 104 has categorized and ranked the one or more potential matches based on the adverse event information and/or the case information of the current case and the one or more potential matching cases, the method 800 proceeds to step 828 at which the provider computing system 104 provides the one or more potential matches to the user computing device 108 for display based on the category and rank. For example and referring to the case duplication page 700, the provider computing system 104 may display or provide the potential matches to the user computing device 108 for display as a likely match or a possible match, with likely matches appearing higher on the user interface (e.g., the case duplication page 700) than possible matches. Further, the provider computing system 104 may order and display the likely matches and the possible matches based on the rank determined at step 824 (e.g., the highest ranking likely matching case is displayed highest, the second highest ranking likely matching case is displayed directly below the highest ranking likely matching case, the lowest ranking likely matching case is displayed directly above the highest ranking possible matching case, the lowest ranking possible matching case is displayed lowest on the case duplication page 700, and so on). In some embodiments, the highest ranking likely matching case is automatically selected (e.g., displayed and represented in the potential matching case comparison section 712) on the user interface.

Once the provider computing system 104 has provided the one or more potential matches to the user computing device 108 for display based on the category and rank, the method 800 proceeds to step 832 at which the provider computing system 104 receives a type of the current case to be generated from the user computing device 108 (and specifically from interaction with the case duplication page 700). As described herein, the type of the case may indicate whether the case is a duplicate case, a follow-up case, or a new case. Further, the type of the case may be provided to the provider computing system 104, in response to the user of the user computing device 108 selecting one of the mark as duplicate button 766, the create follow-up button 770, or the create new case button 774 on the case duplication page 700.

Once the provider computing system 104 has received the type of the current case to be generated from the user computing device 108, the method 800 proceeds to step 836 at which the provider computing system 104 generates the case including the case information based on the type of the case. For example, at step 836, the provider computing system 104 may determine the case to be generated is a new case based on the received case type, and therefore generate the case including the case information and store the case in a database (e.g., in the case database, in the account database 137, etc.). In another example, the provider computing system 104 may determine the case to be generated is a follow-up case based on the received case type, and therefore generate the case including the case information and a link to the original case and store the case in the database.

In some embodiments, at or after step 836, the provider computing system 104 may be configured to provide the case to one or more of the user computing device 108 or the third-party computing system 112. In one example, the case may be stored in the form of an E2B XML file and provided to one or more of the user computing device 108 or the third-party computing system 112 via an AS2 Gateway communication. In some embodiments, the provider computing system 104 may provide the case based on the priority of the case (e.g., a case with priority of one is provided before a case with a priority of two). In other embodiments, the provider computing system 104 may receive an indication or request from the user computing device 108 to provide the case to the third-party computing system 112 and do so in response. In some embodiments, the provider computing system 104 may automatically provide the case based on the timeframe of the case. For example, if the case had a timeframe of seven days from receipt of the source file and it has been seven days from receipt of the source file, the provider computing system 104 may automatically provide the case to one or more of the user computing device 108 or the third-party computing system 112.

The embodiments described herein have been described with reference to the drawings. The drawings illustrate certain details of specific embodiments that implement the systems, methods, and programs described herein. However, describing the embodiments with drawings should not be construed as imposing on the disclosure any limitations that may be present in the drawings.

It should be understood that no claim element herein is to be construed under the provision of 35 U.S.C § 112(f), unless the element is expressly recited using the phrase "means for."

As used herein, the term "circuit" may include hardware structured to execute the functions described herein. In some embodiments, each respective "circuit" may include machine-readable media for configuring the hardware to execute the functions described herein. The circuit may be embodied as one or more circuitry components including, but not limited to, processing circuitry, network interfaces, peripheral devices, input devices, output devices, sensors, etc. In some embodiments, a circuit may take the form of one or more analog circuits, electronic circuits (e.g., integrated circuits (IC), discrete circuits, system on a chip (SOC) circuits), telecommunication circuits, hybrid circuits, and any other type of "circuit." In this regard, the "circuit" may include any type of component for accomplishing or facilitating achievement of the operations described herein. For example, a circuit as described herein may include one or more transistors, logic gates (e.g., NAND, AND, NOR, OR, XOR, NOT, XNOR), resistors, multiplexors, registers, capacitors, inductors, diodes, wiring, and so on.

The "circuit" may also include one or more processors communicably coupled to one or more memory or memory devices. In this regard, the one or more processors may execute instructions stored in the memory or may execute instructions otherwise accessible to the one or more processors. In some embodiments, the one or more processors may be embodied in various ways. The one or more processors may be constructed in a manner sufficient to perform at least the operations described herein. In some embodiments, the one or more processors may be shared by multiple circuits (e.g., circuit A and circuit B may comprise or otherwise share the same processor which, in some example embodiments, may execute instructions stored, or otherwise accessed, via different areas of memory). Alternatively or additionally, the one or more processors may be structured to perform or otherwise execute certain operations independent of one or more co-processors. In other embodiments, two or more processors may be coupled via a bus to enable independent, parallel, pipelined, or multi-threaded instruction execution. Each processor may be implemented as one or more general purpose processors, application specific integrated circuits (ASICs), field programmable gate arrays (FBGAs), digital signal processors (DSPs), or other suitable electronic data processing components structured to execute instructions provided by the memory. The one or more processors may take the form of a single core processor, a multi-core processor (e.g., dual core, quad core, etc.), microprocessor, etc. In some embodiments, the one or more processors may be external to the apparatus. For example, the one or more processors may be a remote processor (e.g., a cloud-based processor). Alternatively or additionally, the one or more processors may be internal and/or local to the apparatus. In this regard, a given circuit or components thereof may be disposed locally (e.g., as part of a local server, a local computing system) or remotely (e.g., as part of a remote server such as a cloud-based server). To that end, a "circuit" as described herein may include components that are distributed across one or more locations. Further, the circuits of the processing circuit described herein may be distributed across one or more locations (e.g., each as part of one or more remote servers).

An example system for implementing the overall system or portions of the embodiments might include a general purpose computing device in the form of computers, including a processing unit, a system memory, and a system bus that couples various system components including the system memory to the processing unit. Each memory device may include non-transient volatile storage media, non-volatile storage media, non-transitory storage media (e.g., one or more volatile and/or non-volatile memories), etc. In some embodiments, the non-volatile storage media may take the form of ROM, flash memory (e.g., flash memory such as NAND, 3D NAND, NOR, 3D NOR), EEPROM, MRAM, magnetic storage, hard disks, optical disks, etc. Combinations of the above are also included within the scope of machine-readable media. In this regard, machine-executable instructions comprise, for example, instructions and data which cause a general purpose computer, special purpose computer, or special purpose processing machine to perform a certain function or group of functions. Each respective memory device may be operable to maintain or otherwise store information relating to the operations performed by one or more associated circuits, including processor instructions and related data (e.g., database components, object code components, script components), in accordance with the example embodiments described herein.

It should also be noted that the term "input devices," as described herein, may include any type of input device including, but not limited to, a keyboard, a keypad, a mouse, a joystick, or other input devices performing a similar function. Comparatively, the term "output device," as described herein, may include any type of output device including, but not limited to, a computer monitor, printer, facsimile machine, or other output devices performing a similar function.

It should be noted that although the diagrams herein may show a specific order and composition of method steps, it is understood that the order of these steps may differ from what is depicted. For example, two or more steps may be performed concurrently or with partial concurrence. Also, some method steps that are performed as discrete steps may be combined, steps being performed as a combined step may be separated into discrete steps, the sequence of certain processes may be reversed or otherwise varied. The order or sequence of any element or apparatus may be varied or substituted according to alternative embodiments. Accordingly, all such modifications are intended to be included within the scope of the present disclosure as defined in the appended claims. Such variations will depend on the machine-readable media and hardware systems chosen and on designer choice. It is understood that all such variations are within the scope of the disclosure. Likewise, software and web implementations of the present disclosure could be accomplished with standard programming techniques with rule-based logic and other logic to accomplish the various database searching steps, correlation steps, comparison steps, and decision steps.

The foregoing description of embodiments has been presented for purposes of illustration and description. It is not intended to be exhaustive or to limit the disclosure to the precise form disclosed, and modifications and variations are possible in light of the above teachings or may be acquired from this disclosure. The embodiments were chosen and described in order to explain the principles of the disclosure and its practical application to enable one skilled in the art to utilize the various embodiments and with various modifications as are suited to the particular use contemplated. Other substitutions, modifications, changes, and omissions may be made in the design, operating conditions and embodiment of the embodiments without departing from the scope of the present disclosure as expressed in the appended claim.

What is claimed is:

1. A method for generating a first case in an adverse event processing system, wherein the adverse event processing system comprises a provider computing system, and a user computing device connected by a secure network, wherein the provider computing system includes a database, the method comprising:

receiving, by a network interface circuit of the provider computing system, adverse event information associated with an adverse event, wherein the adverse event information comprises medical product information associated with a plurality of medical products, reporter information, patient information, and a type of the adverse event;

generating, by a processing circuit of the provider computing system, case information of the first case including the adverse event information, wherein the case information includes a case identifier field, an adverse event field, and a medical product field;

selecting, by the processing circuit, a second case which is a potential duplicate of the first case from the database based on the case information of the first case at least partially matching case information of the second case;

selecting, by the processing circuit, a third case which is a potential duplicate of the first case from the database based on the case information of the first case at least partially matching case information of the third case;

categorizing, by the processing circuit, the second case as a first category of potential duplicate of the first case based on a first number of fields of the case information of the first case matching the first number of corresponding fields of the case information of the second case;

categorizing, by the processing circuit, the third case as a second category of potential duplicate of the first case based on a second number of fields of the case information of the first case matching the second number of corresponding fields of the case information of the third case, wherein the first number is greater than the second number;

providing, by the network interface circuit, the case information of the first case and the second case to the user computing device to be displayed on a user interface, wherein the user interface displays the case information of the first case adjacent to the case information of the second case and includes an identifier comparison section, an adverse event comparison section, a medical product comparison section, a first button selectable to indicate the first case is not a duplicate of the second case and is associated with the second case, and a second button selectable to indicate the first case is not a duplicate of the second case and is not associated with the second case, wherein the identifier comparison section is located below the first button and the second button on the user interface and includes the case identifier field of the first case adjacent to a corresponding case identifier field of the second case, wherein the medical product comparison section is located below the identifier comparison section on the user interface and includes the medical product field of the first case adjacent to a corresponding medical product field of the second case, wherein the adverse event comparison section is located below the medical product comparison section and includes the adverse event field of the first case adjacent to a corresponding adverse event field of the second case;

generating, by the processing circuit and in response to receiving an indication of a selection of the first button via the network interface circuit, the first case including the case information of the first case and a link to the second case; and transmitting, by the network interface circuit, the first case including the case information over the secure network via an Applicability Statement 2 (AS2) communication protocol as an E2B (R2) XML file or an E2B (R3) XML file.

2. The method of claim 1, wherein the adverse event information is received in a source file associated with the adverse event.

3. The method of claim 1, wherein the first category of the second case is provided to the user computing device for display on the user interface.

4. The method of claim 1, wherein the first number is four, wherein the case information of the first case includes a reporter field and a patient field, and wherein categorizing the second case is based on:

1) The medical product field of the first case matching the corresponding medical product field of the second case,
2) The reporter field of the first case matching a corresponding reporter field of the second case,
3) The patient field of the first case matching a corresponding patient field of the second case, and
4) The adverse event field of the first case matching the corresponding adverse event field of the second case.

5. The method of claim 1, wherein the second number is three, wherein the case information of the first case includes a reporter field and a patient field, and wherein categorizing the third case is based on:

1) The medical product field of the first case matching a corresponding medical product field of the third case,
2) The reporter field of the first case matching a corresponding reporter field of the third case, and
3) The patient field of the first case matching a corresponding patient field of the third case.

6. The method of claim 1, wherein the user interface includes a drop down box selectable to drop down a plurality of options, wherein the first button is a first option of the drop down box, wherein the second button is a second option of the drop down box, and wherein the drop down box includes a third option selectable to indicate the first case is a duplicate of the second case.

7. The method of claim 1, wherein the medical product comparison section of the user interface includes a plurality of lines, each line including a field of the case information of the first case and a corresponding field of the case information of the second case.

8. The method of claim 7, wherein at least one line of the plurality of lines includes a visual indicator displayed in the line, in response to the field of the case information of the first case included in the at least one line matching the corresponding field of the case information of the second case.

9. The method of claim 8, wherein the visual indicator includes a color included in the line, wherein the color is at least one of green, yellow, or red.

10. The method of claim 9, wherein the visual indicator includes a checkmark included in the line.

11. A method for generating a first case in an adverse event processing system, wherein the adverse event processing system comprises a provider computing system, and a user computing device connected by a secure network, wherein the provider computing system includes a database, the method comprising:

receiving, by a network interface circuit of the provider computing system, adverse event information associated with an adverse event, wherein the adverse event information comprises medical product information associated with a plurality of medical products, reporter information, patient information, and a type of the adverse event;

generating, by a processing circuit of the provider computing system, case information of the first case including the adverse event information, wherein the case information includes a reporter field, a patient field, and a medical product field;

selecting, by the processing circuit, a second case which is a potential duplicate of the first case from the database based on the case information of the first case at least partially matching case information of the second case;

selecting, by the processing circuit, a third case which is a potential duplicate of the first case from the database based on the case information of the first case at least partially matching case information of the third case;

categorizing, by the processing circuit, the second case as a first category of potential duplicate of the first case based on a first number of fields of the case information of the first case matching the first number of corresponding fields of the case information of the second case;

categorizing, by the processing circuit, the third case as a second category of potential duplicate of the first case based on a second number of fields of the case information of the first case matching the second number of corresponding fields of the case information of the third case, wherein the first number is greater than the second number;

providing, by the network interface circuit, the case information of the first case and the second case to the user computing device to be displayed on a user interface, wherein the user interface displays the case information of the first case adjacent to the case information of the second case and includes a reporter comparisons section, a patient comparison section, a medical product comparison section, a first button selectable to indicate the first case is not a duplicate of the second case and is associated with the second case, and a second button selectable to indicate the first case is not a duplicate of the second case and is not associated with the second case, wherein the reporter comparison section is located below the first button and the second button on the user interface and includes the reporter field of the first case adjacent to a corresponding reporter field of the second case, wherein the patient comparison section is located below the reporter comparison section on the user interface and incudes the patient field adjacent to a corresponding patient field of the second case, wherein the medical product comparison section is located below the patient comparison section on the user interface and includes the medical product field of the first case adjacent to a corresponding medical product field of the second case;

generating, by the processing circuit and in response to receiving an indication of a selection of the first button via the network interface circuit, the first case including the case information of the first case and a link to the second case; and transmitting, by the network interface circuit, the first case including the case information over the secure network via an Applicability Statement 2 (A S2) communication protocol as an E2B (R2) XML file or an E2B (R3) XML file.

12. The method of claim 11, wherein the first category of the second case is provided to the user computing device for display on the user interface.

13. The method of claim 11, wherein the first number is four, wherein the case information of the first case includes an adverse event field, and wherein categorizing the second case is based on:

1) The medical product field of the first case matching the corresponding medical product field of the second case, 2) The reporter field of the first case matching a corresponding reporter field of the second case, 3) The patient field of the first case matching a corresponding patient field of the second case, and 4) The adverse event field of the first case matching a corresponding adverse event field of the second case.

14. The method of claim 11, wherein the second number is three, and wherein categorizing the third case is based on:

1) The medical product field of the first case matching a corresponding medical product field of the third case, 2) The reporter field of the first case matching a corresponding reporter field of the third case, and 3) The patient field of the first case matching a corresponding patient field of the third case.

15. The method of claim 11, wherein the user interface includes a drop down box selectable to drop down a plurality of options, wherein the first button is a first option of the drop down box, wherein the second button is a second option of the drop down box, and wherein the drop down box includes a third option selectable to indicate the first case is a duplicate of the second case.

* * * * *